(12) United States Patent
Tanaka et al.

(10) Patent No.: US 8,574,913 B2
(45) Date of Patent: Nov. 5, 2013

(54) METHOD FOR MEASUREMENT OF HEMOGLOBIN AND HEMOGLOBIN DERIVATIVE, AND MEASUREMENT KIT

(75) Inventors: Hirotaka Tanaka, Ehime (JP); Masanori Tanaka, Osaka (JP)

(73) Assignee: Panasonic Corporation, Osaka (JP)

( * ) Notice: Subject to any disclaimer, the term of this patent is extended or adjusted under 35 U.S.C. 154(b) by 258 days.

(21) Appl. No.: 12/740,857

(22) PCT Filed: Oct. 29, 2008

(86) PCT No.: PCT/JP2008/003081
§ 371 (c)(1),
(2), (4) Date: Apr. 30, 2010

(87) PCT Pub. No.: WO2009/057293
PCT Pub. Date: May 7, 2009

(65) Prior Publication Data
US 2010/0267048 A1    Oct. 21, 2010

(30) Foreign Application Priority Data

Oct. 30, 2007  (JP) .................. 2007-281074
Oct. 31, 2007  (JP) .................. 2007-284123

(51) Int. Cl.
*G01N 33/72* (2006.01)
*G01N 1/00* (2006.01)

(52) U.S. Cl.
USPC ............ 436/67; 436/15; 436/66; 436/177; 436/518; 436/520; 436/522; 436/175; 436/176; 435/7.1; 435/7.25; 435/173.5; 435/173.7; 435/372; 435/378; 422/68.1; 422/73; 422/430

(58) Field of Classification Search
USPC ......... 435/7.1, 7.25, 21, 25, 26, 287.1, 173.5, 435/173.7, 372, 378; 436/8, 15, 66, 67, 436/177, 518, 534, 520, 522, 175, 176; 422/68.1, 73, 430
See application file for complete search history.

(56) References Cited

U.S. PATENT DOCUMENTS 4,448,888 A * 5/1984 Bleile et al. .................. 436/67
4,968,742 A   11/1990 Lewis et al.
5,242,832 A * 9/1993 Sakata ......................... 436/17

(Continued)

FOREIGN PATENT DOCUMENTS

CN    1081765    2/1994
CN    1370276    9/2002

(Continued)

OTHER PUBLICATIONS

International Search Report of PCT/JP2008/003081, dated Jan. 27, 2009.

*Primary Examiner* — Gail R Gabel
(74) *Attorney, Agent, or Firm* — Hamre, Schumann, Mueller & Larson, P.C.

(57) ABSTRACT

Hemoglobin in a sample solution is quickly and reliably denatured; at the same time, quick and accurate measurement of hemoglobin and a hemoglobin derivative is realized. In a method for measuring hemoglobin and a hemoglobin derivative, and a reagent composition, a measurement kit, an analysis device, and an analysis system used in the method, a sample solution containing a blood component is treated with a nonionic surfactant, an oxidizing agent, and a metal salt to denature hemoglobin in the sample solution to measure the hemoglobin, and thereafter the amount of a hemoglobin derivative in the sample is measured by an immunological method using an antibody specifically binding to a denatured site of the denatured hemoglobin derivative.

16 Claims, 10 Drawing Sheets

(56) References Cited

U.S. PATENT DOCUMENTS

| | | |
|---|---|---|
| 5,258,311 A | 11/1993 | Lewis et al. |
| 5,288,606 A | 2/1994 | Siedel et al. |
| 5,541,117 A | 7/1996 | Karl et al. |
| 6,043,043 A * | 3/2000 | Yip .................... 435/7.2 |
| 2005/0145490 A1 | 7/2005 | Shinno et al. |
| 2005/0202399 A1 | 9/2005 | Yonehara et al. |
| 2006/0030050 A1 | 2/2006 | Milne et al. |
| 2008/0293074 A1 | 11/2008 | Tanaka et al. |

FOREIGN PATENT DOCUMENTS

| | | |
|---|---|---|
| EP | 0407860 | 12/1996 |
| EP | 1211505 | 6/2002 |
| EP | 1 873 522 A1 * | 1/2008 |
| EP | 1873522 | 2/2008 |
| JP | 3-051759 | 3/1991 |
| JP | 2002-340895 | 11/2002 |
| WO | 03/104815 | 12/2003 |
| WO | 2006/112339 | 10/2006 |

\* cited by examiner

|  | SAMPLE A | SAMPLE B |
|---|---|---|
| HEMOGLOBIN A1c (g/dl) | 0.66 | 1.32 |
| HEMOGLOBIN (g/dl) | 13.5 | 12.8 |
| RATIO OF HEMOGLOBIN A1c IN ALL HEMOGLOBIN (%) | 4.9 | 10.3 |
| HEMOGLOBIN A1c RATIO MEASURED BY HLC-723GHbV (%) | 5.0 | 10.5 |

METHOD FOR MEASUREMENT OF HEMOGLOBIN AND HEMOGLOBIN DERIVATIVE, AND MEASUREMENT KIT

TECHNICAL FIELD

The present invention relates to a method for measuring hemoglobin and a hemoglobin derivative in a blood sample, a reagent composition, a measurement kit, an analysis device and an analysis system for use in the method, and relates to a technique for more quickly and accurately measuring hemoglobin and a hemoglobin derivative.

Furthermore, the present invention relates to a method for binding a biological substance to a protein. A ligand-protein complex obtained is useful as an agglutinating reagent in immunoassay.

BACKGROUND ART

A hemoglobin derivative, namely, hemoglobin A1c, can be detected in a normal blood glucose level, from which the effect on a blood sugar level (change) by meal is eliminated. Accordingly, hemoglobin A1c is an item frequently measured for early detection of a lifestyle-related disease. Hemoglobin A1c consists of hemoglobin (contained in a red blood cell) and glucose bound to the hemoglobin and is numerically expressed by a ratio (%) of hemoglobin A1c relative to hemoglobin. Therefore, to obtain the ratio of hemoglobin A1c, it is necessary to measure hemoglobin and hemoglobin A1c, separately. Hemoglobin is measured by a method of using light absorption intrinsic of hemoglobin and generally measured near at a wavelength of 415 nm or 540 nm. As a method for measuring hemoglobin near at a wavelength of 540 nm, a cyanmethemoglobin method and an SLS hemoglobin method are widely known. Furthermore, hemoglobin A1c is immunologically measured. For this, hemoglobin has to be taken out of a red blood cell by hemolysis of blood in a sample and the tertiary structure of hemoglobin is changed in order to determine whether the hemoglobin taken out is non-glycated hemoglobin or hemoglobin A1c, thereby exposing a glycated site of hemoglobin out of the tertiary structure. This is called denaturation. Furthermore, the glycated site is allowed to react with an antibody specifically recognizing the glycated site. In this way, the amount of hemoglobin A1c can be immunologically determined.

Note that, as a prior-art document of the present invention, International Publication WO2006/112339 (WO2006/112339A1) is already published. In the publication, a denaturation method for measuring hemoglobin A1c is also disclosed. This method is directed to a method for measuring a hemoglobin derivative by treating a sample containing a blood component with a nonionic surfactant and an oxidizing agent to denature hemoglobin in the sample.

Furthermore, in clinical tests recently performed, various examination methods have been used in order to examine a stage of disease progression. A large scale automatic analyzer, which is capable of quantitatively determining various components in a biological sample, by reacting the biological sample such as blood with analysis reagents, has been used in practice and come to be an indispensable apparatus in the medical field. In the circumstances, lately, it has been commercially desired to develop a more accurate and more universal analyzer including an analysis method reduced in cost, amount of a sample solution, measurement time and size, and enabling simultaneous measurement of many items.

Of the analyzers and analysis methods more universally used, a measurement principle based on an antigen-antibody reaction is generally known, including immunoassays such as immunonephelometry, latex immunoagglutination method, immunoagglutination inhibition method, latex immunoagglutination inhibition method, fluoroimmunoassay, chemiluminescent immunoassay, electrochemical immunoassay, fluorescence polarization immunoassay, and immunochromatography.

In the immunoassay based on a particle agglutination reaction, a specific component in a biological sample is qualitatively and quantitatively measured and determined based on the presence or absence of agglutination of a free anti-analyte antibody or an anti-analyte antibody bound to a water suspensible particle and the degree of agglutination thereof. The water suspensible particle most generally used is a particle called a latex particle.

Of the immunoassays based on the particle agglutination reaction, a measuring method using an immunological particle agglutination inhibition reaction is known. When an anti-analyte antibody and an agglutinating reagent specific to the antibody are mixed, the agglutinating reagent recognizes the anti-analyte antibody to cause agglutination. However, if an analysis object is present in this system, the agglutination is inhibited. Therefore, the analysis-object can be quantitatively detected by optically measuring or counting the degree of agglutination. This measuring method is widely applicable to various types of analysis-objects. In the agglutination reaction, the concentration of an agglutinating reagent has a large effect upon the reaction.

Note that, as an agglutinating reagent used in immunoassay informed in prior-art documents, a ligand-polymer complex is known and generally frequently used (for example, see Japanese Patent Application Laid-Open No. 1-155272). More specifically, the document discloses a ligand-polymer complex, which is an agglutinating reagent for measuring a specific component, particularly, hemoglobin A1c, in a biological sample. The ligand-polymer complex described has a ligand, which is covalently bonded on a polymer material such as polyaspartic acid. FIG. 14 shows an image of a conventional agglutinating reagent formed of a ligand-polymer complex. The conventional agglutinating reagent 4 is composed of a polypeptide (carrier) 5, a linker 2 and a ligand 3 and produced by binding the polypeptide (carrier) 5 to the ligand 3 via the linker 2.

Patent Document 1: International Publication WO2006/112339

Patent Document 2: Japanese Patent Application Laid-Open No. 1-155272

DISCLOSURE OF THE INVENTION

Problem to be solved by the Invention

The method for measuring a hemoglobin derivative previously described uses a nonionic surfactant and an oxidizing agent that have no adverse effect upon an immune reaction. In this method, after hemoglobin is denatured, a latex reagent labeled with an antibody against a hemoglobin derivative is first mixed, and then, mixed with an agglutination polyvalent antigen. In this manner, the hemoglobin derivative can be measured. Herein, to accurately measure the ratio of a hemoglobin derivative in hemoglobin, after all hemoglobin present in a blood sample is denatured without fail, hemoglobin is measured, and then, a hemoglobin derivative has to be measured by an immunological method. In particular, to realize quicker measurement of a hemoglobin derivative, the first denaturation step of hemoglobin has to be efficiently performed in a short time; however, if a reagent having an excessively strong protein denaturing effect is used, an antibody used in the following immunoassay may be damaged. This case should be avoided.

However, according to the method described in the prior art, International Publication WO2006/112339 (WO2006/112339A1) previously described, when a nonionic surfactant and an oxidizing agent, which do not damage an antibody, are used, it takes about 3 minutes to complete the step of denaturing hemoglobin. This is just average time compared to time required for treating hemoglobin with pepsin or an ionic surfactant in a general hemoglobin derivative measuring method. However, to measure a hemoglobin derivative more quickly, it is necessary to reduce the time for denaturing hemoglobin.

Furthermore, according to the method described in Japanese Patent Application Laid-Open No. 1-155272, which is directed to a method for measuring a specific component in a biological sample by immunoassay using a ligand-polymer complex produced by binding a controllable number of ligands and a polymer material, technical improvement such as improvement of sensitivity including reactivity and reproducibility is made, but no consideration is made of time required for the measurement and storage of the ligand-polymer complex at room temperature. In other words, in the conventional immunoassay using a ligand-polymer complex, since an agglutination reaction rate is low, the measurement takes a long time. Furthermore, since the storage at room temperature is unstable, storage in a refrigerator is required.

An object of the present invention is to provide a method for measuring hemoglobin and a hemoglobin derivative, in which hemoglobin and a hemoglobin derivative are more quickly and accurately measured by quickly and reliably denaturing the hemoglobin without having any adverse effect upon an immune reaction to obtain a ratio of the hemoglobin derivative in the hemoglobin. Another object of the present invention is to provide a reagent composition, a measurement kit, an analysis device, and an analysis system used in the aforementioned method.

Furthermore, the present invention solves the aforementioned problems and is directed to reducing the measurement time of a specific component in a biological sample by immunoassay and improving the storage stability of an agglutinating reagent, without having any adverse effect upon an immune reaction.

Means for Solving the Problems

To solve the aforementioned problems, the present invention has an effect of quickly and reliably denaturing hemoglobin while minimizing the effect upon an immune reaction.

Particularly, a method for measuring hemoglobin according to a first aspect of the present invention includes treating a sample containing a blood component with a nonionic surfactant, an oxidizing agent and a metal salt to denature hemoglobin in the sample.

Furthermore, a method for measuring hemoglobin according to a second aspect of the present invention is characterized in that, in the method for measuring hemoglobin according to the first aspect, the metal salt is one of an alkali metal salt and an alkaline earth metal salt.

Furthermore, a method for measuring a hemoglobin derivative according to a third aspect of the present invention includes treating a sample containing a blood component with a nonionic surfactant, an oxidizing agent and a metal salt, followed by measuring hemoglobin in the sample; and performing the immunoassay of a hemoglobin derivative by using an antibody specifically binding to a denatured site of the hemoglobin derivative denatured.

Furthermore, a method for measuring a hemoglobin derivative according to a fourth aspect of the present invention is characterized in that, in the method for measuring a hemoglobin derivative according to the third aspect, the metal salt is one of an alkali metal salt and an alkaline earth metal salt.

Furthermore, a method for measuring a hemoglobin derivative according to a fifth aspect of the present invention is characterized in that, in the method for measuring a hemoglobin derivative according to the third aspect, the concentration of the metal salt is a concentration at which the immunoassay of the hemoglobin derivative is not significantly inhibited.

Furthermore, a method for measuring a hemoglobin derivative according to a sixth aspect of the present invention is characterized in that the method for measuring a hemoglobin derivative according to the third aspect includes measuring the hemoglobin contained in the sample; performing immunoassay of a hemoglobin derivative contained in the sample; and calculating a ratio of the hemoglobin derivative in the hemoglobin.

Furthermore, a method for measuring a hemoglobin derivative according to a seventh aspect of the present invention is characterized in that, in the method for measuring a hemoglobin derivative according to the sixth aspect, the hemoglobin derivative is hemoglobin A1c.

Furthermore, a reagent composition according to an eighth aspect of the present invention, for treating a sample containing a blood component in measuring hemoglobin in the sample, contains at least a nonionic surfactant, an oxidizing agent and a metal salt for denaturing the hemoglobin.

Furthermore, a reagent composition according to a ninth aspect of the present invention is characterized that, in the reagent composition according to the eighth aspect, the metal salt is one of an alkali metal salt and an alkaline earth metal salt.

Furthermore, a reagent composition according to a tenth aspect of the present invention, for treating a sample containing a blood component in measuring hemoglobin and a hemoglobin derivative in the sample, contains at least a nonionic surfactant, an oxidizing agent and a metal salt for denaturing the hemoglobin and the hemoglobin derivative and further contains an antibody specifically binding to a denatured site of the hemoglobin derivative denatured.

Furthermore, a reagent composition according to an eleventh aspect of the present invention is characterized in that, in the reagent composition according to the tenth aspect, the metal salt is one of an alkali metal salt and an alkaline earth metal salt.

Furthermore, a reagent composition according to a twelfth aspect of the present invention is characterized in that, in the reagent composition according to the tenth aspect, the concentration of the metal salt is a concentration at which the immunoassay of the hemoglobin derivative is not significantly inhibited.

Furthermore, a reagent composition according to a thirteenth aspect of the present invention is characterized in that, in the reagent composition according to the tenth aspect, the hemoglobin derivative is hemoglobin A1c.

Furthermore, a measurement kit according to a fourteenth aspect of the present invention for use in measuring hemoglobin in a sample containing a blood component, includes at least a reagent composition containing a nonionic surfactant, an oxidizing agent and a metal salt for denaturing the hemoglobin.

Furthermore, a measurement kit according to a fifteenth aspect of the present invention is characterized in that, in the measurement kit according to the fourteenth aspect, the metal salt is one of an alkali metal salt and an alkaline earth metal salt.

Furthermore, a measurement kit according to a sixteenth aspect of the present invention for use in measuring hemoglobin and a hemoglobin derivative in a sample containing a blood component, includes at least a reagent composition containing a nonionic surfactant, an oxidizing agent and a metal salt for denaturing the hemoglobin and the hemoglobin derivative, and an antibody specifically binding to a denatured site of the hemoglobin derivative denatured by the reagent composition.

Furthermore, a measurement kit according to a seventeenth aspect of the present invention is characterized in that, in the measurement kit according to the sixteenth aspect, the metal salt is one of an alkali metal salt and an alkaline earth metal salt.

Furthermore, a measurement kit according to an eighteenth aspect of the present invention is characterized in that, in the measurement kit according to the sixteenth aspect, the concentration of the metal salt is a concentration at which the immunoassay of the hemoglobin derivative is not significantly inhibited.

Furthermore, a measurement kit according to a nineteenth aspect of the present invention is characterized in that, in the measurement kit according to the sixteenth aspect, the hemoglobin derivative is hemoglobin A1c.

Furthermore, an analysis device according to a twentieth aspect of the present invention for use in measuring hemoglobin in a sample containing a blood component, includes at least a sample addition site for adding the sample; a denaturation section connected to the sample addition site for denaturing the hemoglobin in the added sample with a reagent composition containing a nonionic surfactant, an oxidizing agent and a metal salt; and a detection section connected to the denaturation section for detecting the denatured hemoglobin.

Furthermore, an analysis device according to a twenty-first aspect of the present invention is characterized in that, in the analysis device according to the twentieth aspect, the metal salt is one of an alkali metal salt and an alkaline earth metal salt.

Furthermore, an analysis device according to a twenty-second aspect of the present invention for use in measuring hemoglobin and a hemoglobin derivative in a sample containing a blood component, includes at least a sample addition site for adding the sample; a denaturation section connected to the sample addition site for denaturing hemoglobin in the added sample with a reagent composition containing at least a nonionic surfactant, an oxidizing agent and a metal salt; a detection section connected to the denaturation section for detecting the denatured hemoglobin; and an immunoassay section supporting an antibody specifically binding to a denatured site of a hemoglobin derivative denatured, wherein the hemoglobin derivative in the sample is denatured by the reagent composition, and thereafter, the denatured hemoglobin derivative is detected by immunoassay using the antibody.

Furthermore, an analysis device according to a twenty-third aspect of the present invention is characterized in that, in the measurement kit according to the twenty-second aspect, the metal salt is one of an alkali metal salt and an alkaline earth metal salt.

Furthermore, an analysis device according to a twenty-fourth aspect of the present invention is characterized in that, in the analysis device according to the twenty-second aspect, the concentration of the metal salt is a concentration at which the immunoassay of the hemoglobin derivative is not significantly inhibited.

Furthermore, an analysis device according to a twenty-fifth aspect of the present invention is characterized in that, in the analysis device according to the twenty-second aspect, the hemoglobin derivative is hemoglobin A1c.

Furthermore, an analysis device according to a twenty-sixth aspect of the present invention is characterized in that, in the analysis device according to the twenty-second aspect, the ratio of the hemoglobin derivative in the hemoglobin is calculated.

Furthermore, an analysis system according to a twenty-seventh aspect of the present invention includes the analysis device according to the twenty-second aspect and a measurement section for measuring the amount of the hemoglobin derivative detected by the detection section of the analysis device.

Furthermore, to solve the aforementioned problems, a method for producing an agglutinating reagent according to a twenty-eighth aspect of the present invention is a method in which the controlled number of ligands is chemically bound to a protein having a high-order structure of a molecular weight of 60,000 or more, wherein the ligands are bound to the protein via a linker having a functional group.

Furthermore, a method for producing an agglutinating reagent according to a twenty-ninth aspect of the present invention is characterized in that, in the method for producing an agglutinating reagent according to the twenty-eighth aspect, the protein is a globulin-like protein.

Furthermore, a method for producing an agglutinating reagent according to a thirtieth aspect of the present invention is characterized in that, in the method for producing an agglutinating reagent according to the twenty-eighth aspect, the length of the linker having a functional group is 15 angstroms or less.

Furthermore, a method for producing an agglutinating reagent according to a thirty-first aspect of the present invention is characterized in that, in the method for producing an agglutinating reagent according to the twenty-eighth aspect, the linker has a linear chain structure.

Furthermore, a method for producing an agglutinating reagent according to a thirty-second aspect of the present invention is characterized in that, in the method for producing an agglutinating reagent according to the twenty-eight aspect, the linker has a plane structure.

Furthermore, a method for producing an agglutinating reagent according to a thirty-third aspect of the present invention is characterized in that, in the method for producing an agglutinating reagent according to the twenty-eighth aspect, the ligand is a substance recognizing a specific protein as a binding partner.

Furthermore, a method for producing an agglutinating reagent according to a thirty-fourth aspect of the present invention is characterized in that, in the method for producing an agglutinating reagent according to the twenty-eighth aspect, the ligand is a hapten.

Furthermore, a method for producing an agglutinating reagent according to a thirty-fifth aspect of the present invention is characterized in that, in the method for producing an agglutinating reagent according to the twenty-eighth aspect, the agglutinating reagent is a complex formed of not less than 10 ligands bound to a protein.

Furthermore, an agglutinating reagent or a product according to a thirty-sixth aspect of the present invention is produced by the method for producing an agglutinating reagent according to any one of the twenty-fifth to thirty-fifth aspects.

Furthermore, a method for measuring an analysis object according to a thirty-seventh aspect of the present invention is a method for measuring an analysis object in a test sample by performing particle agglutination control immunoassay, the method including mixing an anti-analyte antibody bound to a water suspensible particle and the test sample to bind the anti-analyte antibody to an analysis object contained in the test sample; mixing a solution, in which the anti-analyte antibody bound to the water suspensible particle and the test sample are mixed, and an agglutinating reagent, which is prepared by chemically binding a ligand having a specific binding site to the anti-analyte antibody to a protein having a high-order structure of a molecular weight of 60,000 or more via a linker having a functional group; agglutinating the anti-analyte antibody unbound to the analysis object contained in the test sample by the agglutinating reagent; and detecting aggregates generated by a reaction between the anti-analyte antibody and the agglutinating reagent to quantify the analysis object in the test sample.

Furthermore, a method for measuring an analysis object according to a thirty-eighth aspect of the present invention is characterized in that, in the method for measuring an analysis object according to the thirty-seventh aspect, the analysis object is hemoglobin A1c, and the ligand is a glycated peptide which corresponds to the peptide sequence of hemoglobin A1c.

Furthermore, a method for measuring an analysis object according to a thirty-ninth aspect of the present invention is characterized in that, in the method for measuring an analysis object according to the thirty-seventh aspect, the agglutinating reagent is used in a region (prozone region), in which an antigen is present in an excessive amount.

Furthermore, a method for measuring an analysis object according to a fortieth aspect of the present invention is characterized in that, in the method for measuring an analysis object according to the thirty-seventh aspect, turbidity due to the aggregates is detected by optical measurement.

Furthermore, a method for measuring an analysis object according to a forty-first aspect of the present invention is characterized in that, in the method for measuring an analysis object according to the thirty-seventh aspect, detection is made by counting the aggregates.

Furthermore, a test kit according to a forty-second aspect of the present invention is a test kit for measuring an analysis object in a test sample by performing particle agglutination control immunoassay, the test kit including an anti-analyte antibody bound to a water suspensible particle, and an agglutinating reagent which is prepared by chemically binding a ligand having a specific binding site to the anti-analyte antibody to a protein having a high-order structure of a molecular weight of 60,000 or more via a linker having a functional group.

Furthermore, a test kit according to a forty-third aspect of the present invention is characterized in that, in the test kit according to the forty-second aspect, the anti-analyte antibody bound to the water suspensible particle and the agglutinating reagent are supported in a dry state.

Furthermore, an analysis device according to a forty-fourth aspect of the present invention is an analysis device for measuring an analysis object in a test sample by particle agglutination control immunoassay, the analysis device including a sample injection section for injecting the test sample; an agglutination section connected to the sample injection section for mixing with the injected test sample an anti-analyte antibody bound to a water suspensible particle and an agglutinating reagent which is prepared by chemically binding a ligand having a specific binding site to the anti-analyte antibody to a protein having a high-order structure of a molecular weight of 60,000 or more via a linker having a functional group to agglutinate the anti-analyte antibody unbound to the analysis object contained in the sample with the agglutinating reagent; and a measurement section connected to the agglutination section for detecting aggregates produced by a reaction between the anti-analyte antibody and the agglutinating reagent to quantify the analysis object in the test sample.

Furthermore, an analysis device according to a forty-fifth aspect of the present invention is characterized in that, in the analysis device according to the forty-fourth aspect, the analysis object is hemoglobin A1c and the ligand is a glycated peptide corresponding to the peptide sequence of hemoglobin A1c.

Furthermore, an analysis device according to a forty-sixth aspect of the present invention is characterized in that, in the analysis device according to the forty-fourth aspect, the agglutinating reagent is used in a region (prozone region), in which an antigen is present in an excessive amount.

Furthermore, an analysis device according to a forty-seventh aspect of the present invention is characterized in that, in the analysis device according to the forty-fourth aspect, one of the anti-analyte antibody bound to the water suspensible particle and the agglutinating reagent is supported in a dry state.

Furthermore, an analysis device according to a forty-eighth aspect of the present invention is characterized in that, in the analysis device according to the forty-fourth aspect, turbidity due to the aggregates is optically detected by the measurement section.

Furthermore, an analysis device according to a forty-ninth aspect of the present invention is characterized in that, in the analysis device according to the forty-fourth aspect, detection is made by counting the aggregates by the measurement section.

Furthermore, an analysis device according to a fiftieth aspect of the present invention is characterized in that, in the analysis device according to the forty-fourth aspect, the measurement section and the agglutination section are integrally formed.

Advantages of the Invention

According to the present invention, hemoglobin can be quickly and reliably denatured by using a nonionic surfactant, an oxidizing agent and a metal salt.

Furthermore, in particular, a nonionic surfactant has the significant characteristics of a small inhibition effect on immunoassay in which a hemoglobin derivative is immunologically measured. By virtue of the characteristics, the operation of diluting a denaturing solution, which is required in denaturing hemoglobin with e.g., an ionic surfactant, is no longer required and thus a reduction in measurement accuracy due to variations in dilution can be eliminated. Furthermore, since the dilution operation is not required, a simpler immunoassay system can be constructed.

In addition, the simultaneous measurement of hemoglobin and a hemoglobin derivative makes it possible to calculate a ratio of a hemoglobin derivative to hemoglobin.

Furthermore, a reagent composition may be in any one of a liquid state, solid state and dried-liquid state as long as the denaturation and measurement of a hemoglobin derivative can be performed by mixing the reagent composition with a sample solution containing a hemoglobin derivative.

Furthermore, since a reagent required for measuring a hemoglobin derivative, a blood sampling device, an instruction manual and so on are packed in a measurement kit, a hemoglobin derivative can be measured more easily even without technical knowledge.

Moreover, since an analysis device supporting a reagent required for measuring a hemoglobin derivative is designed and an analysis system is constructed in combination with a specific analyzer, so that the measurement of a hemoglobin derivative can be simply and quickly performed virtually without being affected by a manual operation.

Furthermore, according to the agglutinating reagent of the present invention, the rate of an agglutination reaction between an anti-analyte antibody bound to a water suspensible particle and an agglutinating reagent which is prepared by chemically binding a ligand having a specific binding site to the anti-analyte antibody to a protein having a high-order structure of a molecular weight of 60,000 or more via a linker having a functional group, increases due to the high-order structure of the protein, with the result that the measurement time of agglutination control immunoassay can be reduced. Furthermore, since the storage stability of the agglutinating reagent is improved, the agglutinating reagent can be stored at room temperature and no longer required to be stored in a refrigerator.

BRIEF DESCRIPTION OF THE DRAWINGS

FIG. 2 (a) is an exploded perspective view of the analysis device and FIG. 2 (b) is a perspective view showing a state of the analysis device to which a reagent is supplied.

FIG. 4 (b) to (d) each show a measurement procedure of the analysis device.

FIG. 5 (a) is the case where KCl is added as a metal salt; FIG. 5 (b) is the case where NaCl is added as a metal salt; and FIG. 5 (c) is the case where $Na_2SO_4$ is added as a metal salt.

FIG. 6 (a) is the case where $MgCl_2$ is added as a metal salt; FIG. 6 (b) is the case where $MgSO_4$ is added as a metal salt; and FIG. 6 (c) is the case where $CaCl_2$ is added as a metal salt.

BEST MODE FOR CARRYING OUT THE INVENTION

Figure 1:
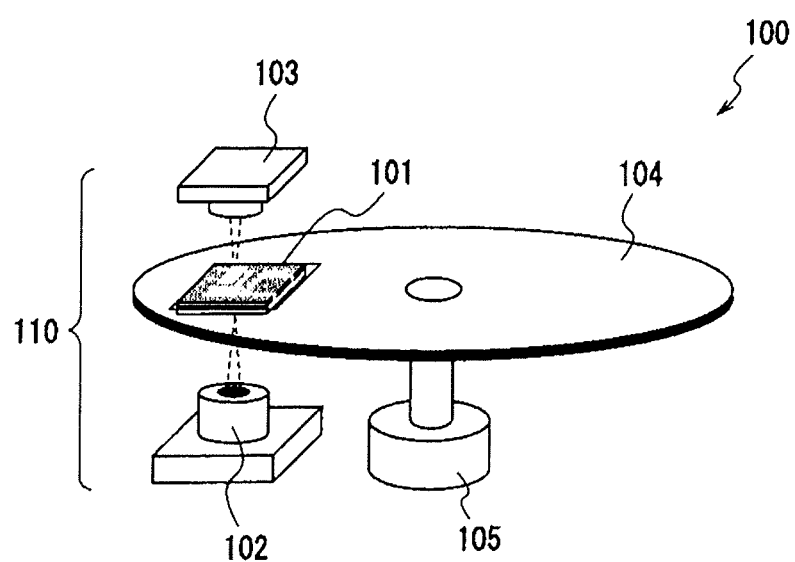
FIG. 1 shows the structure of an analysis system according to Embodiment 4 of the present invention.

A method for measuring hemoglobin or a hemoglobin derivative according to the present invention will be specifically described below.

Embodiment 1

In Embodiment 1 of the present invention, a method for measuring hemoglobin and a method for measuring a hemoglobin derivative including the step of treating a sample containing a blood component with a nonionic surfactant, an oxidizing agent and a metal salt to denature hemoglobin in the sample will be described.

Hemoglobin (hereinafter sometimes referred to as "Hb") is basically a tetramer formed by the association of α-chain and non α-chain (β, γ, δ chains) globins binding to heme. There are a wide variety of hemoglobin including HbA1, which binds to a sugar, acetaldehyde-Hb generated by alcohol intake and carbamylated Hb observed in dialysis patients and so on. Of them, hemoglobin A1c, which has glucose in blood bound to the N terminal of the β-chain thereof, is widely known as an index for a glucose level in the blood over the past 2 to 3 months. As previously mentioned, the hemoglobin derivative of Embodiment 1 refers to hemoglobin partially modified and varied in structure.

Furthermore, when the hemoglobin derivative of Embodiment 1 is measured, it is necessary to distinguish/recognize the regions of a hemoglobin derivative which slightly differ from each other. Individual hemoglobin derivatives have to be identified and quantified. A portion of a hemoglobin derivative different from other hemoglobin derivatives, in other words, a specific site of the hemoglobin derivative is exposed out of the structure of a protein. This is called as "denaturation" in Embodiment 1. The site exposed out of the structure of the protein is called a "denatured site".

In Embodiment 1, the denaturation is performed by using a nonionic surfactant, an oxidizing agent and a metal salt. The oxidizing agent herein oxidizes hemoglobin and converts it into methemoglobin. The nonionic surfactant denatures methemoglobin. The metal salt accelerates these functions. Accordingly, the denaturation of hemoglobin according to the present invention includes the modification of hemoglobin into methemoglobin.

The metal salt is also a reagent playing an important role in the immunoassay of a hemoglobin derivative. More specifically, the steric structure of a protein and an antigen-antibody reaction depend upon a hydrogen bond, electrostatic force, van der Waals' force and hydrophobic bond. To make them function appropriately, a solvent containing a metal salt of an appropriate concentration has to be prepared. Therefore, it is quite important to treat a sample solution at a metal salt concentration so as to have the effect of accelerating the denaturation of hemoglobin and be suitable for an antigen-antibody reaction.

As the aforementioned nonionic surfactant and oxidizing agent, those disclosed in International Publication WO2006/112339 (WO2006/112339A1) can be used. The metal salts include reagents containing metal ions such as Na, K, Mg and Ca. Examples of such reagents include NaCl, KCl, $MgSO_4$, $Na_2SO_4$, $MgCl_2$ and $CaCl_2$, but are not limited to these, as long as the reagent is a metal salt such as an alkali metal salt or an alkaline earth metal salt. Furthermore, the alkali metal salt is a compound consisting of a Group I element, and the alkaline earth metal salt is a compound consisting of a Group II element. Furthermore, the concentration of the metal salt is a concentration at which the immunoassay of a hemoglobin derivative is not significantly inhibited.

Furthermore, in Embodiment 1, "treatment by the use of a nonionic surfactant, an oxidizing agent and a metal salt" indicates that a solution, which is prepared so as to contain a nonionic surfactant, an oxidizing agent and a metal salt which satisfy conditions for obtaining a desired denaturation effect, is added to a sample containing hemoglobin, or indicates that a blood sample is added to a solution, which is prepared so as to contain a nonionic surfactant, an oxidizing agent and a metal salt which satisfy the conditions for obtaining the desired denaturation effect. Note that, when a blood sample is added to a solution containing a nonionic surfactant, an oxidizing agent and a metal salt, the nonionic surfactant has both a denaturation effect and the effect of breaking red blood cell membranes to elute hemoglobin (called "hemolysis").

Furthermore, the treatment methods with a nonionic surfactant, an oxidizing agent and a metal salt include a method of directly adding a solid reagent containing a nonionic surfactant, an oxidizing agent and a metal salt to a sample containing a hemoglobin derivative or a blood sample so as to satisfy conditions for obtaining a desired denaturation effect.

Note that the aforementioned "solid reagent" may be a dry substance. The drying methods include air drying, thermal drying, vacuum drying, vacuum lyophilization, and so on.

As previously described, a sample containing a hemoglobin derivative or a blood sample is treated with a nonionic surfactant, an oxidizing agent and a metal salt to denature hemoglobin in the sample, and then, all hemoglobin is measured near at a wavelength of 540 nm. The denatured hemoglobin derivative is immunologically assayed using an antibody recognizing a region exposed out of the structure of hemoglobin by denaturation. In this manner, the ratio of a hemoglobin derivative to hemoglobin in the sample can be calculated.

A large advantage of the method for measuring a hemoglobin derivative in Embodiment 1 is that immunoassay can be performed using a specific antibody to a denatured site of the hemoglobin derivative treated with a nonionic surfactant, an oxidizing agent and a metal salt while minimizing the effect on an immune reaction. More specifically, in Embodiment 1, since a specific region (denatured site) for determining a hemoglobin derivative can be exposed outside the structure of hemoglobin while minimizing the effect on an immune reaction, measurement can be more specifically performed. In addition, since steric obstruction is reduced in the formation of a complex involved with an antigen-antibody reaction, the efficiency of an antigen-antibody reaction can be improved.

The immunoassay of Embodiment 1 may be any one of immuno-nephelometry, immunonephelometry, latex immunoagglutination method, immunoagglutination inhibition method, latex immunoagglutination inhibition method, fluoroimmunoassay, chemiluminescent immunoassay, electrochemical immunoassay, fluorescence polarization immunoassay and immunochromatography which are generally known, as long as the immunoassay is a measurement principle based on an antigen-antibody reaction.

Of the aforementioned hemoglobin derivatives, the hemoglobin derivative frequently measured is hemoglobin A1c. Hemoglobin A1c serves as an index for controlling diabetes (one of the three major adult diseases which have been at issue recently) and provides an indication of controlling a long-term (1 to 3 months) blood glucose level.

As previously described, according to the method for measuring hemoglobin or a hemoglobin derivative of Embodiment 1, since the step of treating a sample containing a blood component with a nonionic surfactant, an oxidizing agent and a metal salt to denature hemoglobin in the sample is included, the hemoglobin in the sample can be quickly and reliably denatured.

Furthermore, in Embodiment 1, a harmful reagent is not used. Therefore, the measurement of a hemoglobin derivative can be performed more safely. Furthermore, a nonionic surfactant, an oxidizing agent and a metal salt have a less inhibiting effect on an immune reaction. Therefore, when the amount of a hemoglobin derivative is immunologically measured after denaturation treatment, the operation of diluting the solution is not required after the denaturation treatment, with the result that it is possible to prevent a reduction in measurement accuracy caused by dilution and to improve operability for the user. Particularly, a solid reagent consisting of a nonionic surfactant, an oxidizing agent and a metal salt, which is stable in a dry state, is suitably used as an analysis device.

Embodiment 2

Embodiment 2 is directed to a reagent composition which contains at least a nonionic surfactant, an oxidizing agent and a metal salt, for measuring hemoglobin or a hemoglobin derivative. As described in Embodiment 1, as an example of a hemoglobin derivative, hemoglobin A1c is measured.

The reagent composition may be liquid, a mixture of solid substances or a product obtained by drying a liquid reagent composition. Hemoglobin can be denatured simply by mixing the reagent composition with a sample solution containing hemoglobin. Therefore, the reagent composition containing a nonionic surfactant, an oxidizing agent and a metal salt can be the most essential element for simply measuring hemoglobin and a hemoglobin derivative. The metal salt used herein is an alkali metal salt or an alkaline earth metal salt. Furthermore, the concentration of the metal salt is a concentration at which the immunoassay of the hemoglobin derivative is not significantly inhibited.

Furthermore, the nonionic surfactant, oxidizing agent and metal salt, even if they are liquid or solid, may be prepared separately or in a mixture, as long as the three types of reagents can be dissolved in a sample solution at least before hemoglobin is measured.

When the reagent composition is a solution, if it is stored in a refrigerator or protected from light, the stability of the reagent can be further improved.

Note that a dried reagent composition has better storage stability than a liquid reagent composition and can be stored for a long time.

A reagent composition can be dried by processes such as air drying, thermal drying, vacuum drying and vacuum lyophilization. Particularly, in the case of lyophilization, reagent compositions different in design can be produced depending upon the shape of a container for freezing the reagent composition. Furthermore, solubility can be further improved by vacuum lyophilization.

Furthermore, in the case of using potassium ferricyanide as an oxidizing agent, a stable reagent composition for a longer time can be prepared by protecting the reagent composition from light or storing the reagent composition in a dry state.

As previously described, according to the reagent composition for use in the method for measuring hemoglobin or a hemoglobin derivative of Embodiment 2, since the reagent composition contains at least a nonionic surfactant, an oxidizing agent and a metal salt, the denaturation treatment of hemoglobin can be quickly and reliably performed.

Furthermore, since the reagent composition further contains an antibody specific to a denatured site of the hemoglobin derivative, the hemoglobin derivative can be detected by mixing the reagent composition and the sample. Thus, the reagent composition is effective in improving operability for the user.

Embodiment 3

Embodiment 3 is directed to a measurement kit carrying a reagent composition containing at least a nonionic surfactant, an oxidizing agent and a metal salt, and measuring hemoglobin and a hemoglobin derivative with the reagent composition. In this embodiment, as an example of a hemoglobin derivative, hemoglobin A1c is measured as described in Embodiment 1.

The measurement kit includes a reagent and members required for measuring hemoglobin and a hemoglobin derivative. More specifically, the measurement kit includes a reagent required for measuring hemoglobin and a hemoglobin derivative, an instruction manual, members including a blood sampling device such as a lancet or a syringe, disinfectant products required before and after blood sampling and weighing equipment for use in adding the reagent, such as a dispenser and a dropper. The measurement kit is designed such that blood as an examination object is sampled, quantified, diluted and denatured by using the reagent and members. Then, an automatic measuring machine for clinical use or a spectrophotometer, etc. can be used to easily measure hemoglobin and a hemoglobin derivative.

In the measurement kit, processes from the denaturation of hemoglobin to the measurement of hemoglobin are sequentially performed. Therefore, the kit can be easily used even without technical knowledge just by following the instruction manual. Furthermore, the reagent required for measuring hemoglobin and a hemoglobin derivative contains at least a nonionic surfactant, an oxidizing agent and a metal salt. By virtue of the reagent, hemoglobin can be quickly and reliably denatured. In this embodiment, the metal salt is an alkali metal salt or an alkaline earth metal salt. Furthermore, the concentration of the metal salt is a concentration at which the immunoassay of a hemoglobin derivative is not significantly inhibited.

Furthermore, the measurement kit may carry an antibody specific to a hemoglobin derivative. More specifically, the measurement kit may include a reagent composition containing a nonionic surfactant, an oxidizing agent and a metal salt for the hemolysis and denaturation of hemoglobin, a reagent containing an antibody specific to a denatured site of a hemoglobin derivative for detecting the hemoglobin derivative and, for example, when a latex agglutination inhibition reaction is used, an antibody bound to latex (as a label) and an agglutinating reagent serving as an agglutinating polyvalent antigen. The reagents are separately enclosed in containers and the hemolysis and denaturation operation of a hemoglobin derivative and further the immunoassay operation thereof are sequentially performed, so that a hemoglobin derivative can be more easily measured. Note that a latex agglutination inhibition reaction is mentioned as an example but is not limited, as long as hemoglobin is denatured and the amount of a hemoglobin derivative denatured is immunologically measured by using an antibody specific to a denatured site of the hemoglobin derivative.

Furthermore, the measurement kit may include the reagent composition and the antibody separately or the antibody in the reagent composition.

As previously described, according to the measurement kit of Embodiment 3, the reagents required for the measurement of hemoglobin or a hemoglobin derivative in a sample are separately enclosed in containers or collectively enclosed in a container, so that the hemolysis and denaturation of hemoglobin can be performed in accordance with a predetermined procedure and the amount of a hemoglobin derivative denatured can be measured by using a reagent for specifically recognizing the hemoglobin derivative denatured. Therefore, even if the user has no technical knowledge, hemoglobin or a hemoglobin derivative can be more easily measured.

Embodiment 4

Embodiment 4 is directed to an analysis device for detecting hemoglobin and a hemoglobin derivative, the analysis device including at least a sample adding section for adding a sample; a denaturation section for denaturing hemoglobin in the sample with a nonionic surfactant, an oxidizing agent and a metal salt; a detection section for detecting the denatured hemoglobin; and a detection section having an antibody specifically binding to a denatured site of a hemoglobin derivative denatured, for detecting the hemoglobin derivative. In this embodiment, as an example of a hemoglobin derivative, hemoglobin A1c is measured as described in Embodiment 1.

The analysis device can be used in combination with a measuring machine for evaluating the analysis device to configure an analysis system. With this configuration, hemoglobin and a hemoglobin derivative can be measured more easily and quickly.

The analysis device according to Embodiment 4 carries a nonionic surfactant, an oxidizing agent and a metal salt, together with a reagent specific to a denatured site of a hemoglobin derivative and an agglutinating reagent. Furthermore, the device may carry them at separate points thereof.

The metal salt is an alkali metal salt or an alkaline earth metal salt. Furthermore, the concentration of the metal salt is a concentration at which the immunoassay of a hemoglobin derivative is not significantly inhibited.

The measurement is performed in the following order. First, the step of denaturing hemoglobin is performed in which a blood sample is reacted with a nonionic surfactant, an oxidizing agent and a metal salt. Thereafter, the hemoglobin is measured. Then, the step of reacting a hemoglobin derivative denatured, a reagent specific to a denatured site of the hemoglobin derivative, for example, an antibody bound to latex (as a label), which is generated by labeling latex with an antibody specific to a hemoglobin derivative, and an agglutinating reagent is performed.

A sample solution treated with the nonionic surfactant, oxidizing agent and metal salt may be simultaneously reacted with the antibody bound to latex (as a label) and the agglutinating reagent. However, the sample solution may be reacted with the antibody bound to latex (as a label) and thereafter reacted with the agglutinating reagent, or the sample solution may be mixed with the agglutinating reagent and thereafter reacted with the latex reagent.

After the solution is thus reacted with the reagents, a change in the absorbance of the reaction solution is measured to calculate the amount of a hemoglobin derivative.

This makes it possible to calculate the ratio of a hemoglobin derivative to hemoglobin.

It is important for the analysis device to have a shape such that the aforementioned series of reactions and measurement can be smoothly made.

As an example of the analysis device, for example, an analysis device using a centrifugal force and capillary force is conceivable. A liquid sample is freely transferred through chambers (spaces) formed in the analysis device and channels formed between the chambers, so that the order of measurement, the content of a reagent and the reaction time etc., can be controlled. As an example of equipment for evaluating the analysis device configured thus, equipment having a rotation mechanism capable of rotating the analysis device and an optical measurement mechanism capable of measuring absorbance therein is used.

Figure 2A:
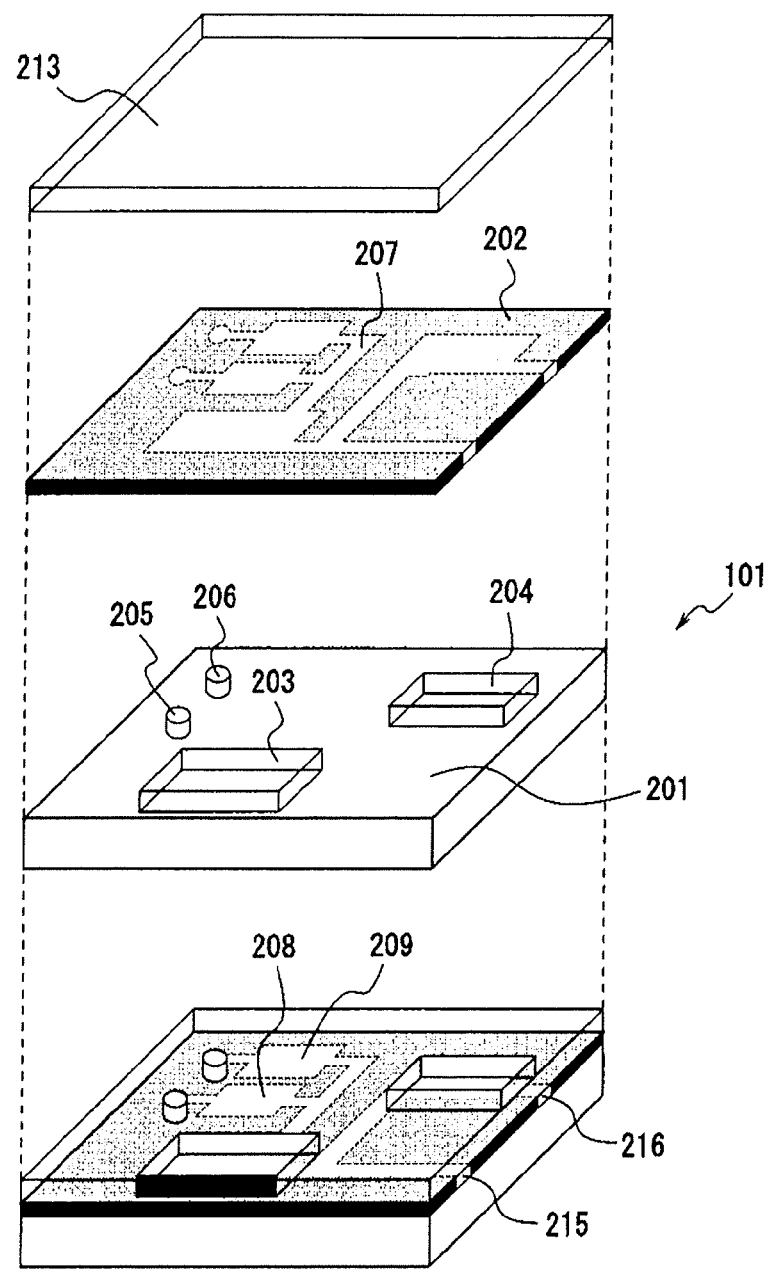
FIG. 2 shows the detailed structure of an analysis device used in the analysis system of FIG. 1 according to Embodiment 4 of the present invention.

Referring to FIG. 1 and FIG. 2A, a structural example of the aforementioned analysis device and analysis system including the analysis device will be described below.

FIG. 1 shows the structure of the analysis system according to Embodiment 4 of the present invention. An analysis system 100 includes a measurement section 110 composed of an analysis device 101, a light source 102 for irradiating the analysis device 101 and a detector 103 for detecting transmitted light, a rotatory substrate 104 having an opened portion into which the analysis device 101 is fixed and a motor 105 for rotating the rotatory substrate 104. Note that, in FIG. 1, a mechanism for driving the motor 105 and the structures of circuits to be connected to the light source 102 and the detector 103 are not shown.

Figure 2B:
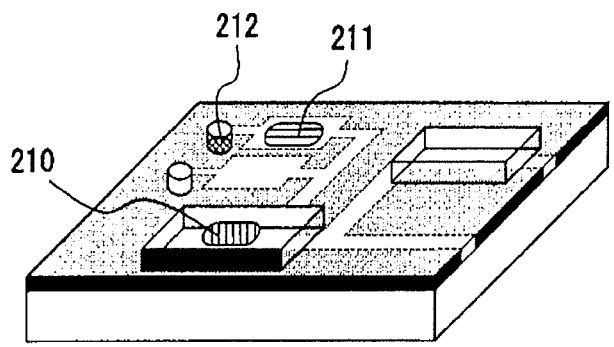

FIG. 2 (*a*) and FIG. 2 (*b*) are views each showing the detailed structure of the analysis device 101. FIG. 2 (*a*) is an exploded perspective view thereof and FIG. 2 (*b*) shows the state of the analysis device to which a reagent is added.

The analysis device 101 has a lower substrate 201, an upper substrate 213 and an adhesive layer 202 having an adhesive effect on both surfaces thereof and is formed by joining them. As the lower substrate 201, a transparent resin substrate is used. Spaces of various shapes are accurately formed by injection molding or the like. More specifically, depressed portions are formed by injection molding on the upper surface of the lower substrate 201, for forming a dilution/stirring section 203 serving as a denaturation site for denaturing a hemoglobin derivative, a diluting-solution storage section 204, a detection section A 205 for detecting the amount of hemoglobin added and a detection section B 206 for detecting the amount of a hemoglobin derivative denatured. Furthermore, as a resin material for the lower substrate 201, any material may be used as long as light can be passed through. By way of example, a plastic resin such as polycarbonate, polystyrene and acryl is used.

Furthermore, in the adhesive layer 202, in addition to patterns corresponding to the dilution/stirring section 203, the diluting-solution storage section 204, the detection section A 205 and the detection section B 206, the patterns of channels 207 connecting the sections are cut out. Furthermore, the channel 207 in front of the detection section A 205 and detection section B 206 is cut out so as to partially expand. Thus, a quantification section A 208 and a quantification section B 209 are formed which quantify the amounts of liquid fed to the detection section A 205 and detection section B 206, respectively. As a material obtaining an adhesive effect of the adhesive layer 202, not only an adhesive but also a hot melt sheet or the like can be used. The hot melt sheet becomes adhesive by heating. The substrate 213 is composed of a transparent resin substrate.

The analysis device 101 is configured as follows. After the lower substrate 201 and the adhesive layer 202 are joined and before the upper substrate 213 is joined, as shown in FIG. 2 (*b*), a denaturing reagent 210 composed of a nonionic surfactant, an oxidizing agent and a metal salt is placed in the dilution/stirring section 203 of the lower substrate 201, a latex reagent 211 capable of specifically reacting with a denatured site of a hemoglobin derivative is placed in the quantification chamber B 209 formed of the lower substrate 201 and the adhesive layer 202, and further an agglutinating reagent 212 composed of a synthetic polyvalent antigen formed by binding a plurality of specific epitope structures of a hemoglobin derivative is placed in the detection section B 206. Thereafter, the resulting structure is dried by vacuum lyophilization and then the upper substrate 213 is joined to the upper surface of the adhesive layer 202. Furthermore, two openings of the channel 207 cut out in the adhesive layer 202 and formed by joining the lower substrate 201, the adhesive layer 202 and the upper substrate 213 in this order, serve as a sample injection port 215 and a diluting-solution injection port 216, respectively.

Next, the operation of the analysis system 100 will be described below.

In analyzing a sample, blood (1 μL) is injected from the sample injection port 215 of the analysis device 101 by using, for example, a dispenser, and at the same time, a diluting solution (500 μL) is injected from the diluting-solution injection port 216. Thus, blood is stored within the channel inside the sample injection port 215 and the diluting solution is stored in the diluting-solution storage section 204.

Next, the analysis device 101 having the blood and the diluting solution injected therein is set in the cut out portions of the rotatory substrate 104. The rotary substrate is rotated by the motor 105 at a predetermined rotation speed for a predetermined time. With this rotation, the diluting solution and blood are transferred to the dilution/stirring section 203, are mixed and serve as a diluted sample solution. The blood in the diluted sample solution is hemolysed by the reaction with a nonionic surfactant, an oxidizing agent and a metal salt and thereafter hemoglobin is denatured.

Next, the rotation of the rotatory substrate 104 is halted, thereby transferring the sample solution through the channel 207 to the quantification section A 208 and the quantification section B 209 by capillary action.

The sample solution transferred to the quantification section B 209 is mixed with the latex reagent 211 previously stored in the quantification section B 209. The latex reagent 211 is bound to a hemoglobin derivative in the sample solution.

Thereafter, when the rotatory substrate 104 is again rotated by the motor 105 at a predetermined rotation speed for a predetermined time, the sample solution transferred to the quantification section A 208 is transferred to the detection section A 205; whereas the sample solution mixed with the latex reagent 211 in the quantification section B 209 is transferred to the detection section B 206.

The agglutinating reagent 212 stored in the detection section B 206 binds to the latex reagent which does not bind to a hemoglobin derivative to cause a latex agglutination inhibition reaction depending upon the concentration of the hemoglobin derivative. After a predetermined time, transmitted light is measured at the detection section B 206 to detect the latex agglutination inhibition reaction.

At the same time, measurement is performed at the detection section A 205, so that the absorption of hemoglobin can be measured and the concentration of hemoglobin can be calculated.

The latex agglutination inhibition reaction can be measured at the detection section B 206 near at a wavelength of 600 nm. Hemoglobin can be measured at the detection section A 205 by measuring hemoglobin absorption near at a wavelength of 540 nm.

In either case, if calibration curves are previously formed based on the measurement results of hemoglobin and a hemoglobin derivative having predetermined concentrations, the concentrations of hemoglobin and the hemoglobin derivative can be obtained by using the calibration curves. The connection between the concentrations of hemoglobin and the hemoglobin derivative is made, so that the ratio of the hemoglobin derivative can be calculated.

In this embodiment, the analysis system having the analysis device 101 in chip-form in which the order of measurement systems, the amount of a reagent, the reaction time and so on are controlled by transferring a liquid with a centrifugal force and capillary force, is described as an example. However, as long as the analysis system has a form such that the order of measurement systems, the amount of a reagent and the reaction time can be controlled, the configuration and method of the analysis system is not limited to those mentioned above. A liquid may be transferred, for example, by a pressure applied by a pump. Furthermore, for the analysis device, for example, chromatography may be employed or more simply, a plastic cell in the form of a rectangular parallelepiped may be employed. In the latter case, it can be sufficiently used by contriving how to store reagents.

Figure 3:
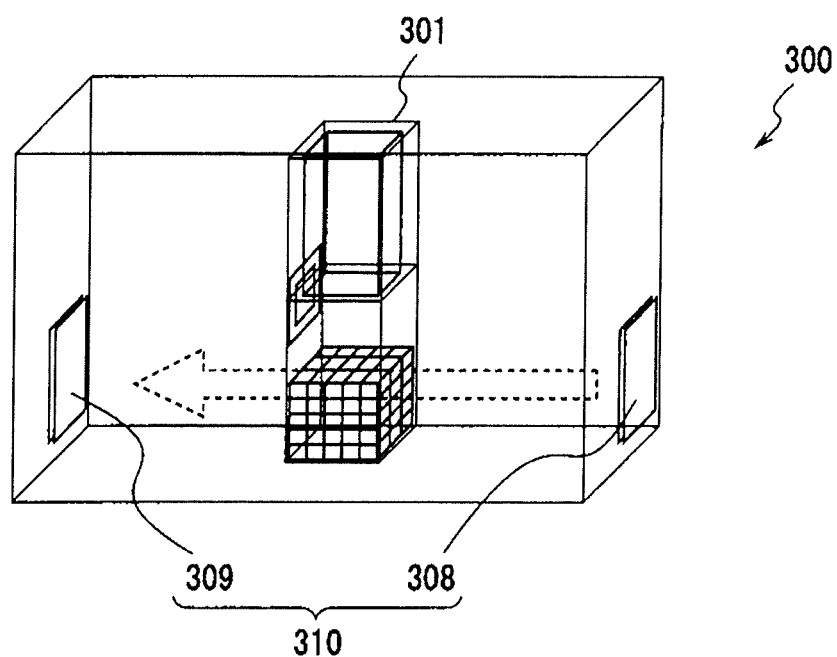
FIG. 3 shows another structure of the analysis system according to Embodiment 4 of the present invention.

Referring to FIG. 3 and FIG. 4, an analysis device having a simpler structure and an analysis system using the analysis device will be described below.

FIG. 3 is a view showing another structure of the analysis system according to Embodiment 4 of the present invention. An analysis system 300 includes a measurement section 310 which consists of a light source 308 for irradiating an analysis device 301 and a light receiving section 309 for detecting transmitted light. Note that, in FIG. 3, a circuit structure for connecting the light source 308 and the light receiving section 309 or a structure for use in installing the analysis device 301 in the analysis system is not shown.

FIGS. 4 (*a*) to (*d*) each show the detailed structure of the analysis device 301. FIG. 4 (*a*) is an exploded perspective view thereof and FIG. 4 (*b*) to (*d*) are views showing the procedure of denaturing treatment with a reagent performed in the analysis device 301.

The analysis device 301 includes a lower case 302*b* with an injection port 306 provided therein for injecting a blood sample, a seal 305 for a reagent solution for sealing the open bottom of the lower case 302*b* closely, an upper case 302*a* and a seal 307 for a case for sealing the injection port 306 closely. The analysis device 301 is formed by joining the open bottoms of the upper case 302*a* and the lower case 302*b* with an adhesive.

The lower case 302*b* is a rectangular parallelepiped case made of plastic with the bottom thereof opened. As shown in FIG. 4B, a reagent 304, which is prepared by adding an antibody specific to a denatured site of the hemoglobin derivative to a reagent consisting of a nonionic surfactant, an oxidizing agent, a metal salt and an agglutinating reagent, is stored closely in the lower case with the seal 305 for a reagent solution.

The upper case 302*a* is substantially the same rectangular parallelepiped case made of plastic with the bottom thereof opened as that of the lower case 302*b*. On the top end of the upper case, as shown in FIG. 4B, a latex reagent 303 capable of specifically reacting with a hemoglobin derivative is lyophilized under vacuum and held.

Next, the operation of the analysis system 300 will be described.

In analyzing a sample, the reagent 304 containing a nonionic surfactant, an oxidizing agent, a metal salt and an agglutinating reagent is injected into the lower case 302*b* by using, for example, a dispenser. The lower case 302*b* is sealed closely with the seal 305 for a reagent solution. Thereafter, as shown in FIG. 4 (*b*), the lower case 302*b* and the upper case 302*a* having the latex reagent are joined with an adhesive. After the seal 305 for a reagent solution is removed, a blood sample (0.5 μL) is injected from the injection port 306 using, for example, a dispenser. Then, as shown in FIG. 4 (*c*), the injection port 306 is sealed closely with the seal 307 for a case. Subsequently, the blood sample and the reagent 304 are gently mixed so as to keep the reagent 304 from coming into contact with the latex reagent 303 held on the top end of the upper case 302*a*, and are left for a predetermined time. Note that, when a hemoglobin concentration is calculated, the analysis device 301 is set in the analysis system 300 at this point, as shown in FIG. 3, and the absorbance near at 540 nm is measured by the measurement section 310.

Next, as shown in FIG. 4 (*d*), the lower case 302*b* of the analysis device 301 is arranged above and the latex reagent 303 is mixed with the reagent 304 having a blood sample added thereto and is left for a predetermined time.

After the passage of the predetermined time, the analysis device 301 is set in the analysis system 300, as shown in FIG. 3, and absorbance is measured near at 600 nm by the measurement section 310 and the concentration of a hemoglobin derivative is calculated.

As previously described, according to the analysis device of Embodiment 4, since the device carries reagents required for the measurement of a hemoglobin derivative, hemoglobin and a hemoglobin derivative can be easily and quickly measured virtually without being affected by a manual operation.

Furthermore, according to the analysis system of Embodiment 4, since the analysis system and the measurement section for the analysis device only are used in combination, hemoglobin and a hemoglobin derivative can be easily and quickly measured virtually without being affected by a manual operation.

Example 1

An example when hemoglobin A1c, which s a typical examination item of a hemoglobin derivative, is measured will be described below.

First, the denaturation of hemoglobin and the measurement of a hemoglobin concentration will be described.

Figure 5A:
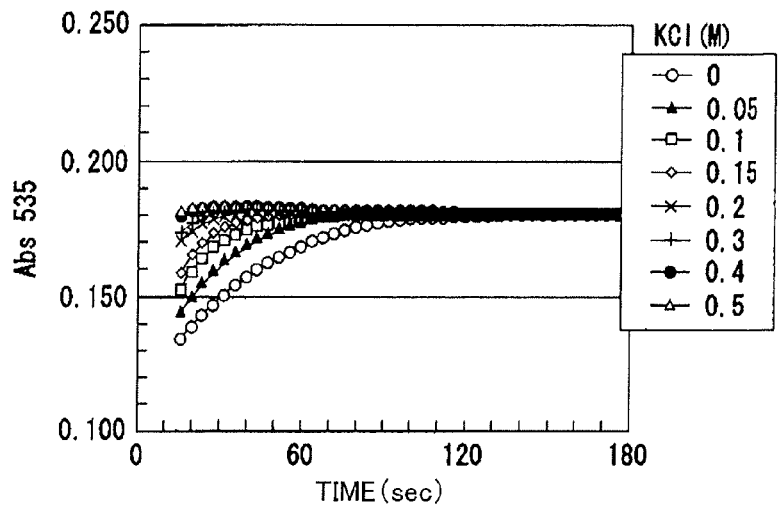
FIG. 5 are graphs showing a change of hemoglobin absorption property with time by adding different types of metal salts to nonionic surfactants and oxidizing agents according to Example 1 of the present invention.
Figure 5B:
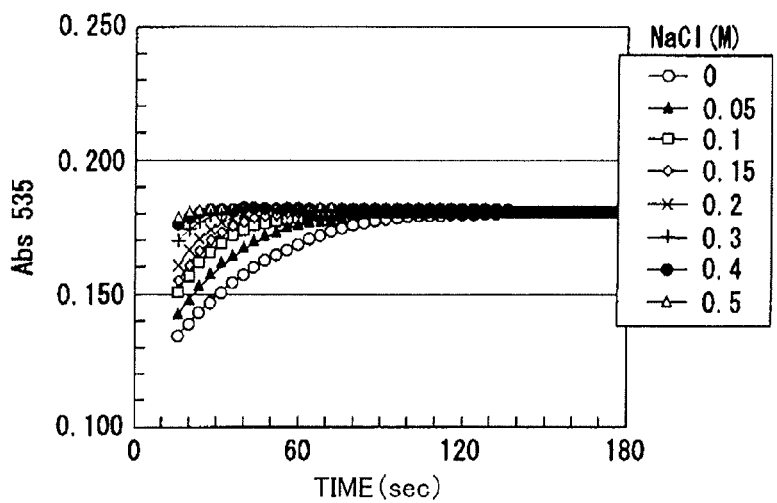
Figure 5C:
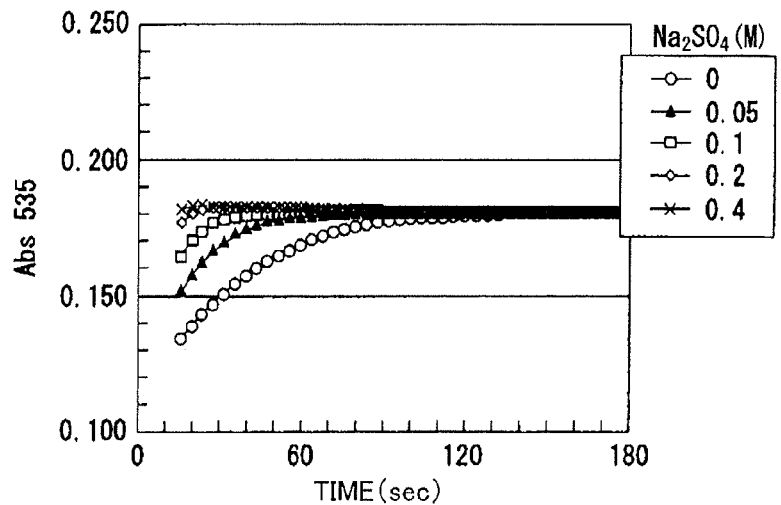
Figure 6A:
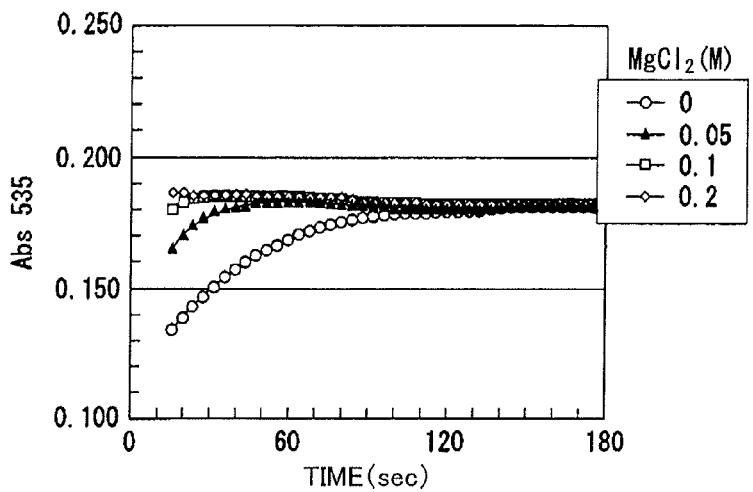
FIG. 6 are graphs showing a change of hemoglobin absorption property with time by adding different types of metal salts to nonionic surfactants and oxidizing agents according to Example 1 of the present invention.
Figure 6B:
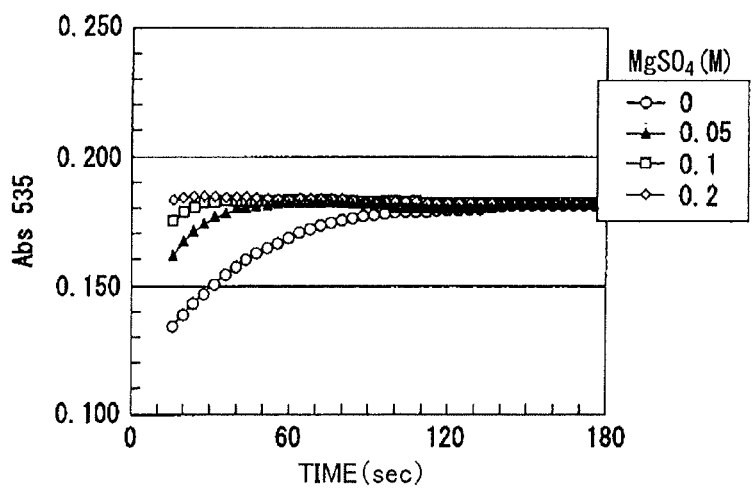
Figure 6C:
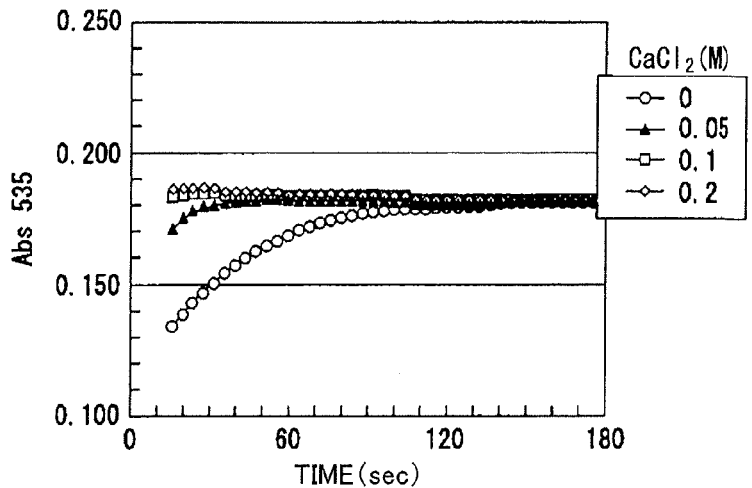

Blood (400 μL) diluted 250 times with purified water and a denaturing reagent (400 μL) having dissolved alkaline metal salts at different concentrations from 0 to 1M in 0.3% sucrose monolaurate and 0.5% potassium ferricyanide were stirred in a plastic cell having an optical path of 1 cm, and a change in the absorbance of hemoglobin was observed at a wavelength of 535 nm over time. The results are shown in FIGS. 5 (*a*) to (*c*) and FIGS. 6 (*a*) to (*c*). According to the results, it was demonstrated that time until the hemoglobin absorbance is stabilized was clearly reduced by adding a metal salt, compared to a case where blood is treated only with sucrose monolaurate and potassium ferricyanide. In a conventional method, about 2 minutes were required until the hemoglobin absorption property was stabilized. In contrast, separately as shown in FIGS. 5 (a) to (c) and FIGS. 6 (a) to (c), it was confirmed that the time until the hemoglobin absorption property is stabilized was reduced by the addition of a salt such as KCl, NaCl, $Na_2SO_4$, $MgCl_2$, $MgSO_4$ and $CaCl_2$ and as the concentration of the salt increases. Furthermore, it was found that the time until the hemoglobin absorption is stabilized varied depending upon the type of a reagent. More specifically, as shown in FIG. 5 (a) where KCl was added, FIG. 5 (b) where NaCl was added and FIG. 5 (c) where $Na_2SO_4$ was added, a concentration of 0.2M or more was required for a monovalent metal salt such as K and Na to stabilize the absorption of hemoglobin within 30 seconds. In contrast, as shown in FIG. 6 (a) where $MgCl_2$ was added, FIG. 6 (b) where $MgSO_4$ was added, FIG. 6 (c) where $CaCl_2$ was added, the hemoglobin absorption was stabilized within 30 seconds at a concentration of Mg (0.1 M) and Ca (0.05 M). It was found that Ca and Mg, which are divalent metal salts, were effective in stabilizing the hemoglobin absorption at a lower concentration than a monovalent metal salt.

Figure 7:
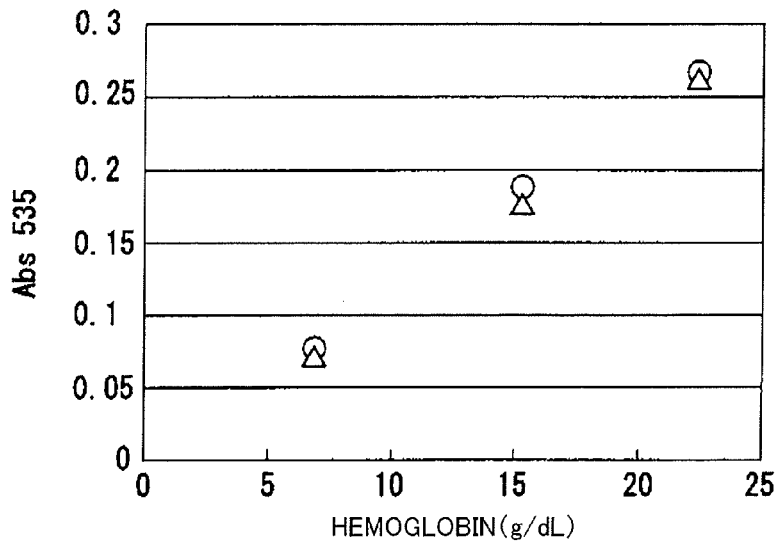
FIG. 7 shows the relationship between hemoglobin and absorption property with respect to an SLS-hemoglobin method and a treating method with a nonionic surfactant, an oxidizing agent and a metal salt according to Example 1 of the present invention.

A sample having a known hemoglobin concentration was measured for the concentration of hemoglobin at 535 nm by using an SLS-hemoglobin method, namely, "Hemoglobin B Test Wako" (manufactured by Wako Pure Chemical Industries Ltd.). The same sample was treated with 0.15% sucrose monolaurate, 0.25% potassium ferricyanide and 0.2 M NaCl, and after 30 seconds, hemoglobin was measured at 535 nm. The two methods were compared. As a result, as shown in FIG. 7, a highly excellent correlation was confirmed. From the aforementioned results, it was found that hemoglobin was quickly denatured by adding a metal salt to sucrose monolaurate and potassium ferricyanide, with the result that the time until the hemoglobin absorption property is stabilized was reduced and the measurement of hemoglobin could be accurately realized equivalently to the measurement by the SLS-hemoglobin method.

Example 2

Next, the effect of a metal salt upon a latex agglutination reaction was determined.

Figure 8:
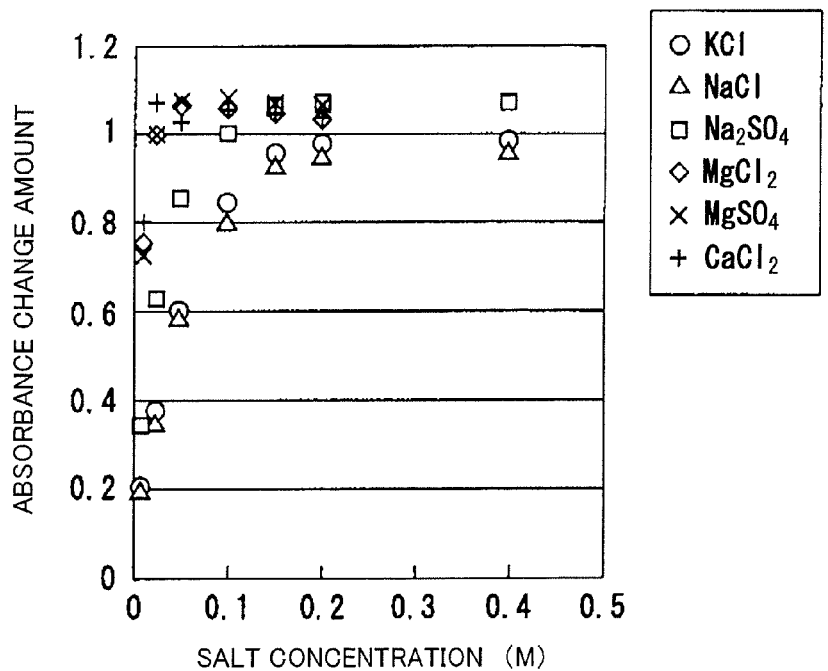
FIG. 8 is a view showing the effect of a metal salt upon an immune reaction according to Example 2 of the present invention.

To a latex reagent solution containing 0.15% sucrose monolaurate and 0.25% potassium ferricyanide, KCl, NaCl, $Na_2SO_4$, $MgCl_2$, $MgSO_4$ and $CaCl_2$ different in concentration were added. Thereafter, to the mixture, an agglutinating reagent consisting of an agglutination polyvalent antigen was added. One minute later, the absorbance was measured at 550 nm and the variation was obtained. The results are shown in FIG. 8.

According to the results, it was found that the reactivity of the latex agglutination reaction increased as the concentration of a metal salt increased and the reactivity became stable when the salt concentration reached a predetermined level or more. Particularly, at a salt concentration at which the hemoglobin absorption property immediately becomes stable, no decrease in agglutination reactivity was found and no adverse effect of a metal salt upon an immune reaction was found. From the aforementioned results, it was found that a hemoglobin derivative could be accurately measured without inhibiting the immunoassay system by adding a metal salt to sucrose monolaurate and potassium ferricyanide.

Example 3

The measurement of hemoglobin and a hemoglobin derivative using the analysis system shown in FIG. 3 will be described below.

(a) Production of Analysis Device

First, as shown in FIG. 4 (a), an upper case 302a made of plastic with the bottom thereof opened which is 0.5 cm long× 0.5 cm wide×2 cm high is prepared. On the top end of the upper case, as shown in FIG. 4 (b), a latex reagent 303 consisting a latex reagent capable of specifically binding to hemoglobin A1c and a solution containing 5% sucrose, is supported by vacuum lyophilization.

Figure 4A:
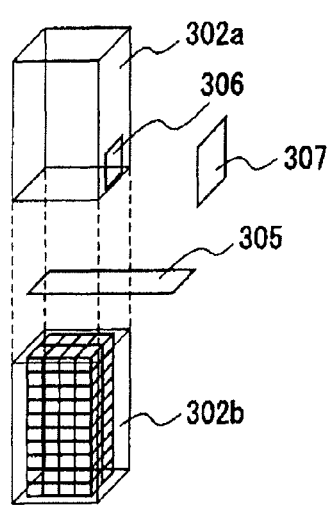
FIG. 4 shows the detailed structure of an analysis device used in the analysis system of FIG. 3 according to Embodiment 4 of the present invention, FIG. 4 (a) is an exploded perspective view of the analysis device.
Figure 4B:
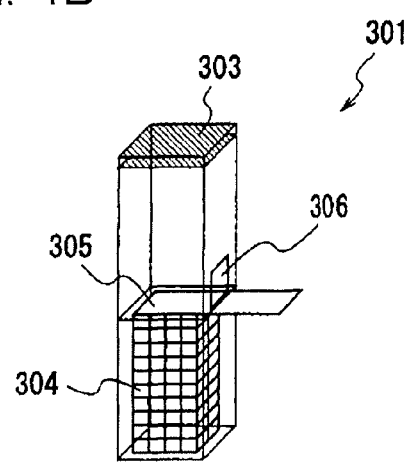
Figure 4C:
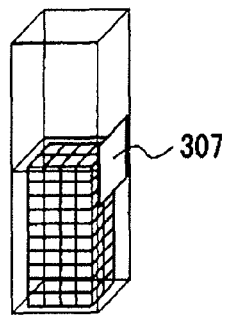
Figure 4D:
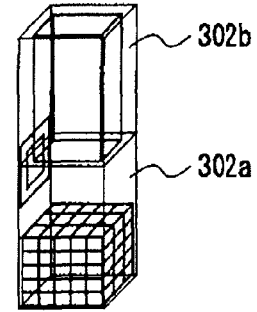

Next, to a lower case 302b, as shown in FIG. 4(a), made of plastic with the same shape as that of the upper case 302a, as shown in FIG. 4 (b), a reagent 304 which is a solution (0.2 mL) containing 0.15% sucrose monolaurate, 0.25% potassium ferricyanide and 0.15M sodium chloride, and a synthetic polyvalent hemoglobin A1c antigen serving as an agglutinating reagent are injected. After the lower case is sealed with a seal 305 for a reagent solution, the upper case 302a and the lower case 302b are joined with an adhesive such that the opened bottoms face each other to form an analysis device 301.

(B) Analysis

First, the seal 305 for a reagent solution is removed. Then, a blood sample (0.5 μL) is injected from an injection port 306 of the analysis device 301. As shown in FIG. 4 (c), a seal 307 for a case is attached to the injection port 306 to seal the analysis device 301 closely.

Next, the blood sample and the reagent 304 are gently mixed so as to keep the reagent 304 from coming into contact with the latex reagent 303 supported on the upper case 302a and left in this state for 30 seconds. Thereafter, as shown in FIG. 3, the analysis device 301 is set in an analysis system 300 and the absorbance is measured at 535 nm by the measurement section 310.

Next, as shown in FIG. 4 (d), the analysis device 301 is inverted to mix and dissolve the latex reagent 303 on the upper case 302a and the reagent 304. Thereafter, as shown in FIG. 3, the analysis device 301 is set within the analysis system 300. One minute after the latex reagent 303 is dissolved, the absorbance is measured at 550 nm by the measurement section 310.

Detailed description of the measurement section 310 will be omitted. Light is applied from a light source 308 to the analysis device 301 and the transmitted light is detected by a light receiving section 309. Note that, as an example of the measurement section 310, one having the function of a spectrophotometer can be sufficiently used and therefore, the detailed description will be omitted. Note that, cyanmethemoglobin is measured at 535 nm and latex agglutination is measured at 550 nm. The series of measurement operations are repeated on two types of blood samples A and B.

Thereafter, the absorbance values obtained as described above are assigned to the calibration curve of cyanmethemoglobin and the calibration curve of latex agglutination inhibition reaction of hemoglobin A1c, which are previously obtained using a hemoglobin solution and a hemoglobin A1c solution having a known concentration by means of the analysis system 300, to obtain the hemoglobin concentration and hemoglobin A1c concentration of each of the blood samples A and B.

Figures 9, 10:
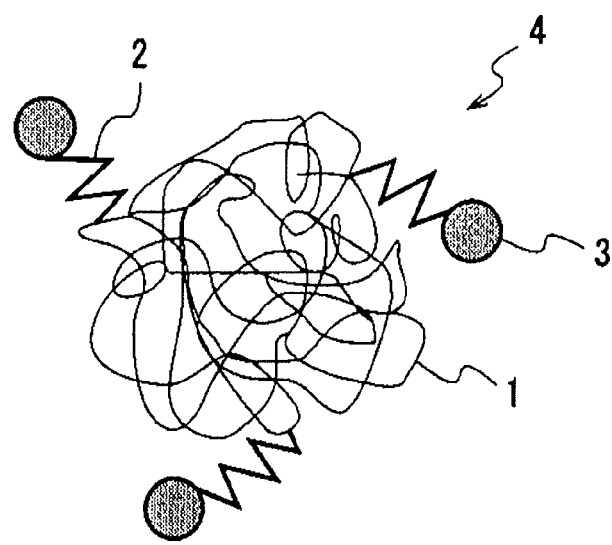
FIG. 9 is a view showing the measurement results of blood samples A, B by an analysis system according to Example 3 of the present invention and by an automatic analyzer for glycated hemoglobin.
FIG. 10 is a view showing an image of an agglutinating reagent according to the present invention.

FIG. 9 shows the hemoglobin A1c concentration and hemoglobin concentration and further the ratio of hemoglobin A1c with respect to each of the blood samples A and B.

As shown in FIG. 9, the ratios of hemoglobin A1c measured by the analysis system 300 are 4.9 in the blood sample A, and 10.3 in the blood sample B, which are very close to the ratios of hemoglobin A1c previously measured by an automatic glycated hemoglobin analyzer (HLC-723 GHbV) manufactured by Tosoh Corporation, that is, 5.0 in the blood sample A and 10.5 in the blood sample B, respectively. It was demonstrated that the concentration of hemoglobin A1c could be accurately measured by the analysis system 300.

Next, embodiments of a method for manufacturing an agglutinating reagent and a method for measuring an analysis object using the agglutinating reagent according to the present invention and a test kit and an analysis device thereof will be more specifically described.

Embodiment 5

A method for manufacturing an agglutinating reagent and a method for measuring hemoglobin A1c using the agglutinating reagent in Embodiment 5 of the present invention will be described.

A. Production of Ligand

The ligand of the present invention may be any substance as long as it can recognize a specific protein as a binding partner. A typical example thereof is a hapten. In Embodiment 5, as a glycated peptide corresponding to a peptide sequence in hemoglobin A1c, a peptide having an amino acid sequence of valine-histidine-leucine-threonine-cysteine (hereinafter referred to as VHLTC) is used as a ligand for an agglutinating reagent. The ligand can specifically bind to an antibody recognizing hemoglobin A1c. Furthermore, if the ligand is altered, ligands which specifically recognize various types of antibodies can be produced.

B. Production of Agglutinating Reagent

The agglutinating reagent of the present invention is obtained by chemically binding the controlled number of ligands to a protein having the high-order structure of a molecular weight of 60,000 or more, via a linker having a functional group. Furthermore, the agglutinating reagent is a complex having not less than 10 ligands bound to a single protein.

The protein may be any protein as long as it has a molecular weight of 60,000 or more. Typical examples of the protein include, but are not limited to, globulin-like proteins such as gamma globulin, thyroglobulin and albumin. More desirably, a protein having a molecular weight of about 60,000 to 300,000 is preferred.

The reason why a protein having a molecular weight of 60,000 or more is preferred is as follows. Since a protein having a molecular weight of less than 60,000 has a small number of amino groups, which serve as a site to be chemically bound to a linker, not less than 10 ligands cannot bind, with the result that the agglutination reactivity of a water suspensible particle disadvantageously decreases. In contrast, since a protein having a molecular weight of 60,000 or more has a large number of amino groups, which serve as a site to be chemically bound to a linker, not less than 10 of ligands can bind, with the result that the agglutination reactivity of a water suspensible particle advantageously increases.

The length of the linker having a functional group is desirably 15 angstroms or less. The linker may be any desired linker as long as it has a functional group, and a linker having a linear structure or a planar structure may be used. Typical examples of the linker include N-(6-Maleimidocaproyloxy)succinimide (hereinafter referred to as EMCS), Succinimidyl-trans-4-(N-maleimidylmethyl)cyclohexane-1-carboxylate (hereinafter referred to as SMCC) and N-succinimidy(4-iodoacetyl)aminobenzoate (hereinafter referred to as SIAB).

FIG. 10 shows an image of the agglutinating reagent according to Embodiment 5 of the present invention.

In FIG. 10, an agglutinating reagent 4 of the present invention is composed of a protein (carrier) 1 having a molecular weight of 60,000 or more, a linker 2 having a functional group and a ligand (VHLTC) 3. The agglutinating reagent 4 is produced by allowing the ligand (VHLTC) 3 to bind to the protein (carrier) 1 via the linker 2 having a functional group. At this point, about twenty ligands 3 are allowed to bind to a single carrier. The ligands 3 recognize and bind to specific antibodies. When an antibody binds to not less than two ligands 3 of a single agglutinating reagent, the antibodies mutually bind via the agglutinating reagent. Agglutination proceeds sequentially.

The ligand-protein complex thus produced is used as an agglutinating reagent for immunoassay.

C. Production of an Antibody Bound to Latex (as a Label)

To a polystyrene latex particle, an excessive amount of anti-human HbA1c antibody is added, bounded and further blocked with bovine serum albumin (hereinafter referred to as BSA) to produce an antibody bound to latex (as a label). The anti-human HbA1c antibody recognizes and binds to hemoglobin A1c in a test sample and the ligand (VHLTC) 3 of the agglutinating reagent. Furthermore, if the antibody is replaced with other types of antibodies, antibodies bound to latex (as a label) capable of recognizing various components in test samples and agglutinating reagents can be produced.

D. Measurement of Analysis Object in Test Sample by Latex Immunoagglutination Inhibition Method To measure hemoglobin and hemoglobin A1c in a blood sample, first, the blood sample is diluted. The diluted blood sample is mixed with a denaturing reagent containing a non-ionic surfactant and an oxidizing agent to convert hemoglobin in the blood sample into methemoglobin and denature the hemoglobin. By conversion of hemoglobin into methemoglobin, the absorbance of hemoglobin can be measured at 540 nm. Thereafter, the absorbance of the diluted and denatured sample is measured near at a wavelength of 540 nm to calculate the total amount of hemoglobin using a methemoglobin method. Note that other hemoglobin measurement methods such as an SLS hemoglobin method may be used.

Next, to measure hemoglobin A1c, the denatured sample is added to an antibody bound to latex (as a label), i.e., an anti-human HbA1c antibody. An antigen-antibody reaction occurs between the anti-human HbA1c antibody bound to latex and a denatured site of hemoglobin A1c in the blood sample. Thereafter, to the sample reacted with the antibody bound to latex (as a label), the agglutinating reagent is added. The agglutinating reagent binds to the remaining anti-human HbA1c antibody unbound to hemoglobin A1c in the blood sample. As a result, an agglutination reaction continuously occurs at a site to which the agglutinating reagent binds to generate aggregates. The amount of aggregates generated in the reaction solution increases in inverse proportion to the concentration of hemoglobin A1c. This reaction is called as a latex immunoagglutination inhibition reaction.

Next, after the passage of predetermined time, the turbidity of the reaction solution due to the aggregates generated therein is detected by optical measurement. For the detection, the absorbance (A) of a measurement section is measured. Furthermore, before the agglutinating reagent is added, the blank absorbance (A1) of the measurement section is measured beforehand. Based on the difference (A−A1) between these values of absorbance, a change in absorbance is calculated $$\text{Change in absorbance} = A - A1$$

Based on the change in absorbance, the amount of hemoglobin A1c in the blood sample is calculated.

From the results, the amount of hemoglobin A1c relative to hemoglobin in the blood sample, in other words, the ratio thereof can be obtained.

$$\text{Hemoglobin } A1c \text{ concentration (\%) in blood sample} = \frac{\text{Hemoglobin } A1c \text{ concentration (mg/dL)}}{\text{Hemoglobin concentration (mg/dL)}} \times 100 \quad \text{[Formula 1]}$$

According to Embodiment 5, the agglutinating reagent is produced by chemically binding the controlled number of ligands to a protein having a high-order structure of a molecular weight of 60,000 ore more via a linker having a functional group. Therefore, owing to the high-order structure of the protein, the rate of an agglutination reaction between anti analysis-object antibodies bound to water suspensible particles can be increased and the measurement time of agglutination control immunoassay can be reduced. Furthermore, since the agglutinating reagent is improved in storage stability and can be stored at room temperature, storage in a refrigerator is no longer required.

Embodiment 6

In Embodiment 6 of the present invention, a test kit having at least an agglutinating reagent, an antibody bound to latex (as a label) and a denaturing reagent to measure hemoglobin and hemoglobin A1c by these reagents will be described.

The test kit includes reagents and members required for measuring hemoglobin and hemoglobin A1c. More specifically, the test kit includes reagents required for measuring hemoglobin and hemoglobin A1c, an instruction manual, members including a blood sampling device such as a lancet or a syringe, disinfectant products required before and after blood sampling, and weighing equipment for use in adding the reagents, such as a dispenser and a dropper. The test kit is designed such that a blood sample serving as an examination object is taken, quantified, diluted and denatured by using the reagents and members and then hemoglobin and hemoglobin A1c can be easily measured using an automatic measuring machine for clinical use or a spectrophotometer, etc.

In the test kit, processes from blood sampling to measurement are sequentially performed. Therefore, it is possible to easily use the kit just by following the instruction manual even without any technical knowledge. Furthermore, the reagent required for measuring hemoglobin and hemoglobin A1c is a reagent containing at least an agglutinating reagent, an antibody bound to latex (as a label) and a denaturing reagent. Hemoglobin A1c can be quickly and reliably measured by the reagent.

Furthermore, the antibody bound to latex (as a label) and the denaturing reagent may be separately held in the test kit or the denaturing reagent may be contained in the antibody bound to latex (as a label).

As previously described, according to the test kit of Embodiment 6 of the present invention, all the reagents required for measuring hemoglobin A1c in a sample are respectively contained in containers, etc. Therefore, the user can easily measure hemoglobin and hemoglobin A1c in accordance with the predetermined procedure.

Embodiment 7

In Embodiment 7 of the present invention, an analysis device for measuring hemoglobin and hemoglobin A1c will be described. The analysis device is constituted by at least an injection port for injecting an analysis sample; a diluting-solution storage chamber for storing a diluting solution; a dilution/denaturation chamber for diluting and denaturing the injected analysis sample; a hemoglobin measuring chamber for detecting diluted and denatured hemoglobin; a latex reaction chamber for reacting the diluted and denatured analysis sample with an antibody bound to latex (as a label); an agglutination chamber for reacting the analysis sample reacted with the antibody bound to latex (as a label) with an agglutinating reagent; and a measurement chamber for measuring an analysis object in the analysis sample.

The analysis device can be set in combination with a measuring machine for evaluating the analysis device to configure an analysis system. With this configuration, hemoglobin A1c can be easily and quickly measured.

The analysis device of Embodiment 7 has an agglutinating reagent, an antibody bound to latex (as a label) and a denaturing reagent at separate sites thereof.

A measuring method by the analysis device of Embodiment 7 will be described below.

First, a blood sample and a denaturing reagent are mixed to dilute/denature the blood sample. Thereafter, the diluted and denatured blood sample is irradiated with light having a predetermined wavelength to measure all hemoglobin. Next, the diluted and denatured blood sample and an antibody bound to latex (as a label) are mixed to cause an antigen-antibody reaction. The blank absorbance of a measurement section is measured. Thereafter, the mixture solution is mixed with an agglutinating reagent to agglutinate anti analysis-object antibodies with each other. The absorbance of the aggregate generated by the agglutination is measured. Using values obtained by the measurements and the formula of Embodiment 5, hemoglobin A1c is calculated. Based on the measurement of hemoglobin and hemoglobin A1c, the amount of hemoglobin A1c relative to hemoglobin in the sample, in other words, the ratio thereof is calculated. Thus, a concentration can be detected.

Note that a blood sample can be diluted and denatured, and simultaneously reacted with an antibody bound to latex (as a label) to cause an antigen-antibody reaction.

It is important for the analysis device to have a shape such that the series of reactions and measurements previously mentioned are smoothly performed.

As an example of the analysis device, a device using, for example, a centrifugal force and capillary force is conceivable. The order of measurement, the content of a reagent, reaction time and so on can be controlled by freely transferring a liquid sample through a plurality of chambers (space) formed in the analysis device and channels formed between the chambers.

As an example of an apparatus for evaluating the analysis device configured thus, an apparatus including a rotation mechanism capable of rotating the analysis device and a member with an optical measurement function capable of measuring absorbance is mentioned.

Referring to FIG. 1 and FIG. 2, a configuration example of the analysis device and a configuration example of the analysis system including the analysis device will be described below.

FIG. 1 shows the structure of the analysis system. An analysis system 100 is constituted by a measurement section 110 including an analysis device 101, a light source 102 for irradiating the analysis device 101 and a detector 103 for detecting transmitted light; a rotatory substrate 104 having an opened portion for fixing the analysis device 101; and a motor 105 for rotating the rotatory substrate 104. Note that, in FIG. 1, a mechanism for driving the motor 105 and circuit structures connected to the light source 102 and the detector 103 are not shown.

FIG. 2 is a view showing the detailed structure of the analysis device. FIG. 2 (a) is an exploded perspective view thereof and FIG. 2 (b) is a view showing the state of the analysis device to which a reagent is added.

The analysis device 101 is formed by joining a lower substrate 201 and an upper substrate 213 with an adhesive layer 202 having an adhesive effect on both surfaces thereof. As a material for the substrates, a transparent resin substrate is used. Spaces with various shapes are accurately formed by injection molding or the like. To be specific, depressed portions used for forming a dilution/denaturation chamber 203 serving as a dilution/denaturation site of a sample, a diluting-solution storage chamber 204, a detection section A 205 for detecting hemoglobin in the sample and a detection section B 206 for detecting hemoglobin A1c, are formed in the upper surface of the lower substrate 201 by injection molding. Note that, as a resin material for the upper substrate 213 and the lower substrate 201, a plastic resin such as polycarbonate, polystyrene and acryl may be used. The resin material is not limited to these. Any resin material can be used as long as it can transmit light.

Furthermore, in the adhesive layer 202, in addition to the patterns of the dilution/denaturation chamber 203, the diluting-solution storage chamber 204, the detection section A 205 and the detection section B 206, the patterns of channels 207 connecting these chambers and sections are cut out. Furthermore, the channel 207 in front of the detection section A 205 and detection section B 206 is cut out so as to partially expand. Thus, a quantification section A 208 and a quantification section B 209 are formed to quantify the amount of liquid to be fed to the detection section A 205 and detection section B 206, respectively. As a material having an adhesive effect of the adhesive layer 202, not only an adhesive but also a hot melt sheet or the like can be used. The hot melt sheet becomes adhesive by heating.

The analysis device 101 is formed as follows. After the lower substrate 201 and the adhesive layer 202 are joined and before the upper substrate 213 is joined, as shown in FIG. 2 (b), a denaturing reagent 210 is supported in the dilution/denaturation chamber 203 of the lower substrate 201, an antibody bound to latex (as a label) 211 is supported in the quantification chamber B 209 formed of the lower substrate 201 and the adhesive layer 202, and further an agglutinating reagent 212 is supported in the detection section B 206. Thereafter, the device is dried and then the upper substrate 213 is joined to the upper surface of the adhesive layer 202. Furthermore, two openings of the channel 207 cut out in the adhesive layer 202 and formed by joining the upper substrate 213, the adhesive layer 202 and the lower substrate 201, serve as a sample injection port 215 and a diluting-solution injection port 216, respectively.

The operation of the analysis system 100 will be described below.

In analyzing a sample, blood (1 μL) is injected from the sample injection port 215 of the analysis device 101 using, for example, a dispenser, and at the same time, a diluting solution (500 μL) is injected from the diluting-solution injection port 216. The blood is stored within the channel inside the sample injection port 215 and the diluting solution is stored in the diluting-solution storage chamber 204.

Next, the analysis device 101 having blood and the diluting solution injected therein is set in the cut-out portion of the rotatory substrate 104. The substrate is rotated by the motor 105 at a predetermined rotation speed for a predetermined time. Owing to the rotation, the diluting solution and blood are transferred to the dilution/denaturation chamber 203, and mixed to be a diluted sample solution. Hemoglobin is converted into methemoglobin and denatured with a denaturing reagent.

Next, the rotation of the rotatory substrate 104 is halted, thereby transferring the sample solution containing hemoglobin converted into methemoglobin and denatured through the channel 207 to the quantification section A 208 and the quantification section B 209 with the help of capillary action.

The sample solution containing hemoglobin converted into methemoglobin and denatured and having been transferred to the quantification section B 209, is mixed with the latex reagent 211 previously stored in the quantification section B 209. Hemoglobin A1c contained in the sample solution binds to the latex reagent 211.

Thereafter, the rotatory substrate 104 is again rotated by the motor 105 at a predetermined rotation speed for a predetermined time. The sample solution containing hemoglobin converted into methemoglobin and denatured and having been transferred to the quantification section A 208, is transferred to the detection section A 205; whereas the sample solution mixed with the latex reagent 211 in the quantification section B 209 is transferred to the detection section B 206.

The agglutinating reagent 212 supported in the detection section B 206 binds to the latex reagent unbound to hemoglobin A1c to cause a latex agglutination inhibition reaction depending upon the concentration of hemoglobin A1c. After a predetermined time, transmitted light is measured at the detection section B 206 to detect the latex agglutination inhibition reaction.

At the same time, measurement is performed at the detection section A 205. Thus, the absorption of hemoglobin is measured and a hemoglobin concentration is calculated.

The latex agglutination inhibition reaction can be measured in the detection section B 206 near at a wavelength of 600 nm. Hemoglobin can be measured in the detection section A 205 by measuring the absorption of hemoglobin near at a wavelength of 540 nm.

In either case, if calibration curves of hemoglobin and hemoglobin A1c are previously formed based on the measurement results of the hemoglobin and the hemoglobin A1c having predetermined concentrations, the concentrations of hemoglobin and hemoglobin A1c can be obtained using the calibration curves. Based on the concentrations, a ratio of hemoglobin A1c can be calculated.

In this embodiment, the analysis system having the analysis device 101 in the form of a chip, in which the order of measurement systems, the amount of a reagent, reaction time and so on are controlled by transferring a liquid with the help of a centrifugal force and capillary force, is mentioned as an example. However, as long as the analysis system has a form such that the order of measurement systems, the amount of a reagent, reaction time and so on can be controlled, the structure and method of the analysis system are not limited to those previously mentioned. A liquid may be sufficiently transferred, for example, with a pressure applied by a pump. Furthermore, as the analysis device, for example, chromatography may be employed or more simply, a plastic cell in the form of a rectangular parallelepiped may be employed. In the latter case, it can be sufficiently used by contriving how to store reagents.

As previously described, according to Embodiment 7, the analysis device supporting reagents required for the measurement of hemoglobin A1c is designed. Simultaneously, the analysis system is constructed by using the analysis device and a measurement section for the analysis device only in combination. Therefore, hemoglobin A1c can be simply and quickly measured virtually without being affected by a manual operation.

Example 4

An example of a method for producing an agglutinating reagent and an antibody bound to latex (as a label) will be specifically described below.

The agglutinating reagent was produced by using chicken gamma globulin (hereinafter referred to as CGG) as a carrier, EMCS as a linker and VHLTC as a ligand. The N terminal of EMCS and the cysteine of VHLTC were bound and further the C terminal of EMCS and the amino group of CGG were bound to produce the agglutinating reagent. At this time, about 20 VHLTC sequences were bound to a single CGG.

Furthermore, an antibody bound to latex (as a label) was produced by adding an excessive amount of anti-human HbA1c antibody to polystyrene latex particles (manufactured by Sekisui Chemical Co., Ltd.) having an average particle size of 0.12 µm to bind together by physical adsorption. To the resultant latex particle-antibody complex, 0.5% bovine serum albumin (hereinafter referred to as BSA) was added to perform blocking. In this way, the antibody bound to latex (as a label) was prepared. Note that the particle diameter of latex is not limited to the aforementioned. Any particle may be used as long as it has a diameter of 0.05 µm to 1.0 µm Example 5

An example of a method for producing a second agglutinating reagent will be specifically described below.

The agglutinating reagent was produced by using IgY (obtained by purifying only immunoglobulin G which is the main component of CGG) as a carrier, EMCS as a linker and VHLTC as a ligand. The N terminal of EMCS and the cysteine of VHLTC were bound and further the C terminal of EMCS and the amino group of IgY were bound to produce the agglutinating reagent. At this time, about 20 VHLTC sequences were bound to a single IgY. Since variation from lot to lot of the carrier of the agglutinating reagent is small compared to variation in using CGG as a carrier, an agglutinating reagent can be produced with a small variation from lot to lot.

Example 6

An example of a method for measuring an analysis object in a test sample by a latex immunoagglutination inhibition method will be specifically described below.

First, blood (400 µL) diluted 250 times with purified water and a denaturing reagent (400 µL) containing 0.30 sucrose monolaurate and 0.5% potassium ferricyanide were mixed to convert hemoglobin in the blood into methemoglobin and denature the hemoglobin. Note that a reagent used in the step of converting hemoglobin into methemoglobin and denaturing it is not limited to this. Any reagent may be used as long as it contains a nonionic surfactant and an oxidizing agent. The diluted and denatured blood was measured for the absorbance thereof at a wavelength of 535 nm and a total hemoglobin concentration was calculated.

Next, to measure hemoglobin A1c, the diluted and denatured blood was added to the antibody bound to latex (as a label) of Example 1 lyophilized under vacuum to cause an antigen-antibody reaction. The reaction solution was added to the agglutinating reagent of the present invention lyophilized under vacuum and an agglutination reaction was caused at 37° C. Note that vacuum lyophilization was employed to prepare the antibody bound to latex (as a label) and agglutinating reagent; however, any method such as air drying, thermal drying and vacuum drying may be used as long as it produces a dry substance. Furthermore, the agglutinating reagent according to the present invention does not inhibit an immune reaction and is fundamentally equivalent to a conventional agglutinating reagent in an antigen-antibody reaction.

To detect turbidity due to aggregates by optical measurement, absorbance (A) was measured at a wavelength of 625 nm. Furthermore, before the agglutinating reagent was added, absorbance (A1) was measured at a wavelength of 625 nm. Based on a difference in absorbance value, a change (A−A1) in absorbance was calculated.

If the calibration curves of hemoglobin and hemoglobin A1c are previously formed based on the measurement results of hemoglobin and hemoglobin A1c having predetermined concentrations, the concentrations of hemoglobin and hemoglobin A1c can be calculated based on the calibration curves. Based on the concentrations, the ratio of hemoglobin A1c was calculated.

Comparative Example

A comparative experiment was performed using an agglutinating reagent of the preset invention, which is composed of CGG as a carrier, EMCS as a linker and VHLTC as a ligand, and a conventional agglutinating reagent, which is composed of polylysine as a carrier, EMCS as a linker and VHLTC as a ligand.

Figure 11:
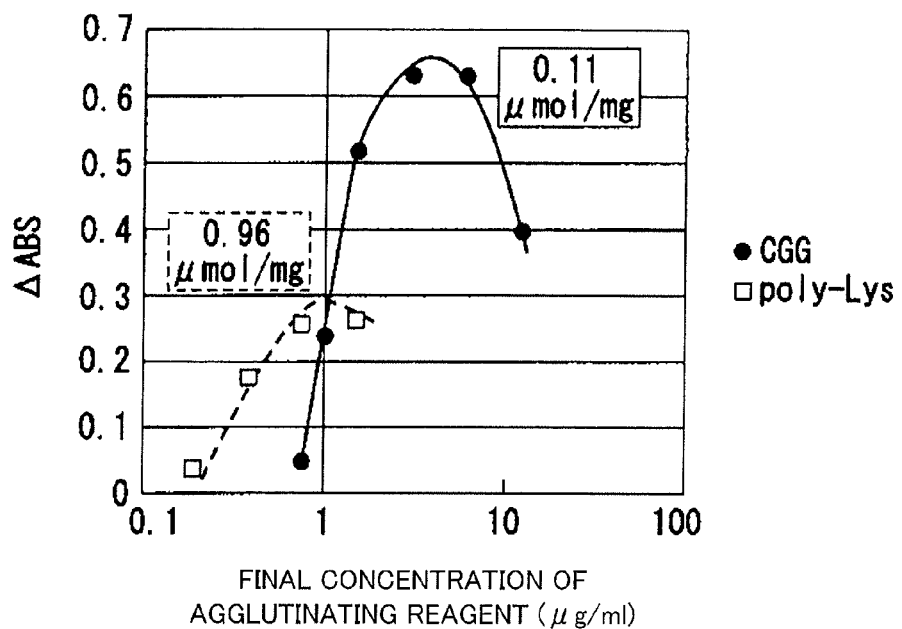
FIG. 11 is a graph showing the relationship between the concentration of the agglutinating reagent and a change in absorbance.

(a) Relationship Between Concentration of Agglutinating Reagent and Absorbance Change FIG. 11 shows the relationship between a change in absorbance measured and the concentration of an agglutinating reagent added in a latex agglutination reaction caused between an antibody bound to latex (as a label) and the agglutinating reagent. The horizontal axis shows the concentration of the agglutinating reagent. The vertical axis shows a change in absorbance one minute after the addition of the agglutinating reagent. According to FIG. 11, both in the conventional agglutinating reagent and the agglutinating reagent of the present invention, as the concentration of the agglutinating reagent increases, the amount of aggregates increases and the measurement value of absorbance increases. When the concentration of the agglutinating reagent exceeds a predetermined level, that is, the maximum value of an absorbance change, an antigen is excessively present in the reaction solution. Therefore, the formation of an aggregate is suppressed and conversely, the measurement value of absorbance apparently decreases. For example, the measurement value of absorbance of the conventional agglutinating reagent decreases in the concentration range of 1 µg/mL or more, whereas the measurement value of absorbance of the agglutinating reagent according to the present invention decreases in the concentration range of 5 µg/mL or more. The range is generally called a prozone region and the phenomenon is called a prozone phenomenon. If an agglutinating reagent is used within the concentration range, the effect of the concentration variation of the agglutinating reagent upon reactivity can be reduced. Furthermore, since the agglutinating reagent is excessively present, the rate of the agglutination reaction can be increased. From the results, it was found that the dynamic range of the agglutinating reagent of the present invention is larger. Since the dynamic range is large, the inclination of a calibration curve becomes large, with the result that the accuracy of measurement is improved.

Furthermore, regarding the amount of ligand per carrier of the agglutinating reagent used at this time, the amount of ligand of the agglutinating reagent (CGG) according to the present invention was 0.11 µmol/mg, and that of the conventional agglutinating reagent (poly-Lys) was 0.96 µmol/mg.

(b) Change of Agglutination-Reaction Completion Rate with the Passage of Time in the Prozone-Region Concentration of Agglutinating Reagent.

Figure 12:
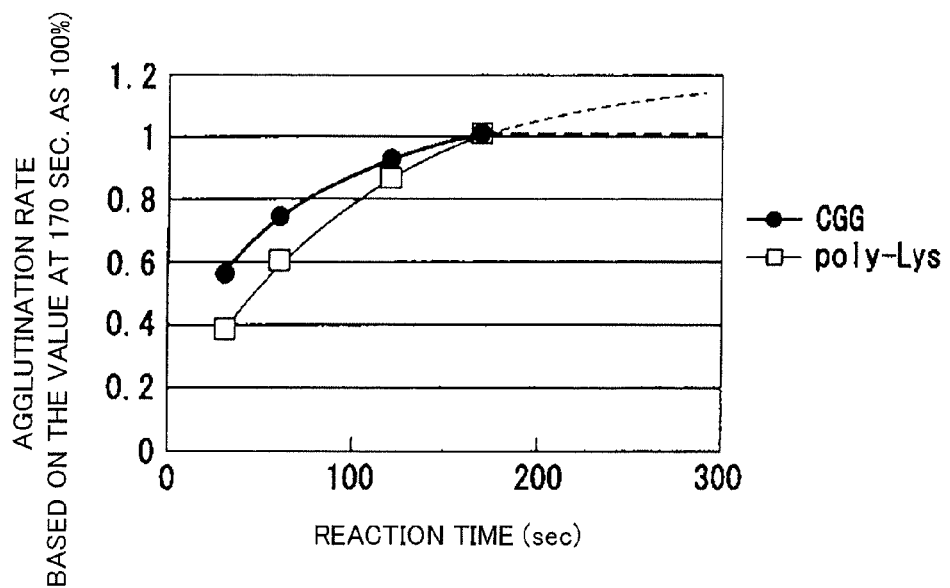
FIG. 12 is a graph showing differences in agglutination rate depending upon the type of the agglutinating reagent.

FIG. 12 shows a change in the agglutination-reaction completion rate with time in the latex agglutination inhibition reaction using the agglutinating reagent within the prozone-region concentration. The horizontal axis indicates the time after the agglutinating reagent is added. The vertical axis indicates the agglutination-reaction completion rate provided that an agglutination completion rate reaches 100% 170 seconds after the agglutinating reagent is added. As shown in FIG. 12, in the case where the agglutinating reagent of the present invention is used, the absorbance becomes stable after 170 seconds. Whereas, in the case where the conventional agglutinating reagent is used, as is apparent from the inclination of a graph, the reaction still proceeds even after 170 seconds and the absorbance increases. Provided that the agglutination completion rate reaches 100% after 170 seconds, it is apparent that the agglutination rate and the agglutination-reaction completion rate are higher in the agglutinating reagent of the present invention. This is clear from a comparison made, for example, 60 seconds after the start of agglutination. The agglutination-reaction completion rate of the conventional agglutinating reagent is 60%, whereas the agglutination-reaction completion rate of the present invention is 75%.

From the results, it is found that when the agglutinating reagent of the present invention is used, the agglutination reaction proceeds at a higher rate and is completed in a shorter time. In the assay in which the agglutinating reagent of the present invention is used, the agglutination reaction is completed within 3 minutes after it starts. On the other hand, when the conventional agglutinating reagent is used, about twice as long as the time is required until the agglutination reaction is completed to the same degree.

(c) Storage Stability of Agglutinating Reagent

Figure 13:
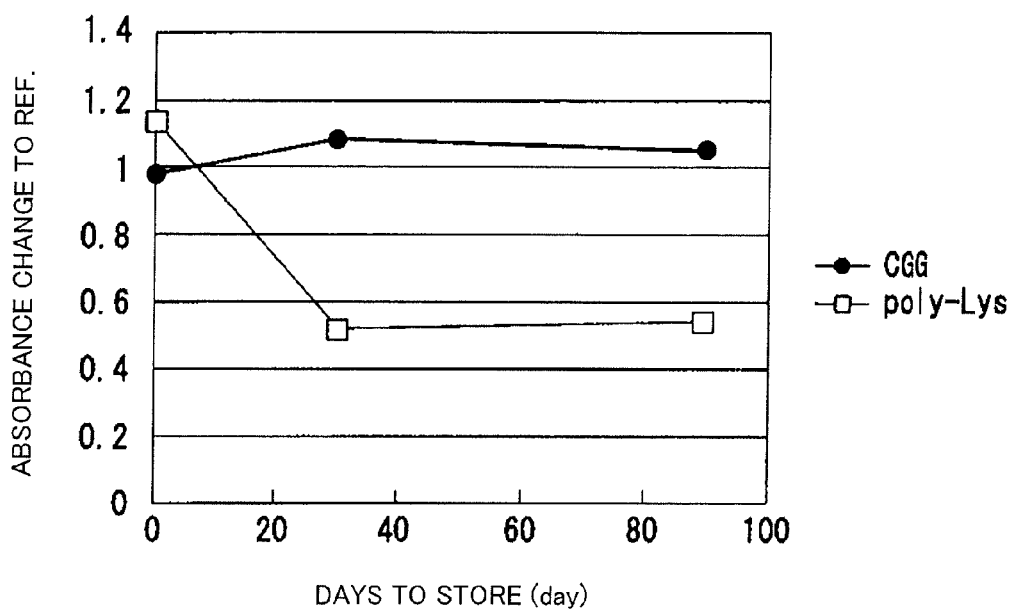
FIG. 13 is a graph showing differences in storage stability depending upon the type of the agglutinating reagent.
Figure 14:
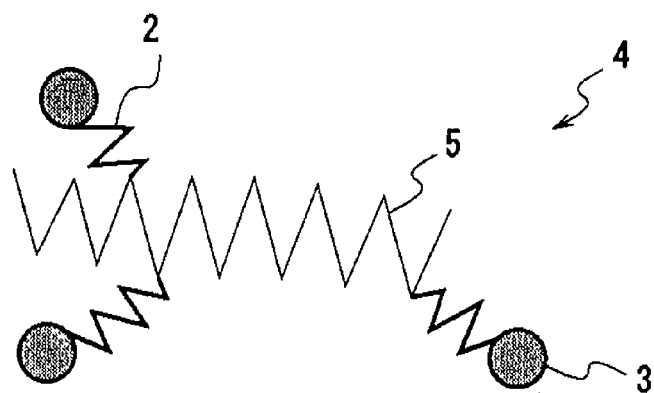
FIG. 14 is a view showing an image of a conventional agglutinating reagent.

FIG. 13 shows the storage stability of an agglutinating reagent. The agglutinating reagent was lyophilized under vacuum and stored in an environment of 40° C. Using the agglutinating reagent, a latex agglutination inhibition reaction was caused. The absorbance was measured using a spectrometer. Based on a difference in absorbance before and after the reaction, the reactivity of the agglutinating reagent was confirmed. The horizontal axis indicates days to store the agglutinating reagent. The vertical axis indicates the absorbance change rate relative to a reference at the time when the agglutination reaction is measured. Note that, as a reference, an agglutinating reagent cryopreserved at −80° C. was used. As shown in FIG. 13, the conventional agglutinating reagent having been stored for 3 months shows a change in absorbance, which is only about a half of that of the reference; whereas the agglutinating reagent of the present invention having been stored for 3 months shows a change in absorbance almost equivalent to that of the reference. It is found that the reactivity is likely to be stable.

From the results, it was observed that the reactivity of the conventional agglutinating reagent stored at 40° C. decreased in a month. In comparison, the agglutinating reagent of the present invention stored at 40° C. exhibits satisfactory storage stability in 3 months. It was found that the storage stability clearly improved.

Note that the experiment was performed using a spectrometer (U2800) manufactured by Hitachi Ltd.

INDUSTRIAL APPLICABILITY

According to the present invention, since hemoglobin in a sample solution can be denatured quickly and reliably, hemoglobin and a hemoglobin derivative can be quickly and accurately measured.

Furthermore, according to the present invention, since agglutination reaction time can be reduced, measurement can be performed quickly and accurately; at the same time, the storage stability of an agglutinating reagent increases. Therefore, the agglutinating reagent can be stored at room temperature, thereby simplifying the handling of a sample piece to be analyzed in immunoassay.

The invention claimed is:

1. A method for measuring hemoglobin, comprising:
   treating a sample containing a blood component including red blood cells with a nonionic surfactant, an oxidizing agent and a metal salt to denature hemoglobin in the sample, and
   performing an optical measurement of methemoglobin generated from treating the sample with the nonionic surfactant, the oxidizing agent and the metal salt so as to determine an amount of the hemoglobin in the sample, wherein the metal salt is present in an amount sufficient to accelerate the denaturation of the hemoglobin and includes at least one metal ion selected from the group consisting of sodium (Na), potassium (K), magnesium (Mg) and calcium (Ca).

2. A method for measuring a hemoglobin derivative, comprising:
   treating a sample containing a blood component including red blood cells with a nonionic surfactant, an oxidizing agent and a metal salt for denaturing so as to allow measurement of the hemoglobin and hemoglobin A1c as a hemoglobin derivative,
   performing an optical measurement of the hemoglobin in the sample,
   performing an immunoassay of the hemoglobin A1c as a hemoglobin derivative by using an antibody specifically binding to a denatured site of the hemoglobin A1c as a hemoglobin derivative denatured, and
   determining an amount of the hemoglobin derivative in the sample based on an amount of binding of the antibody to the denatured site of the hemoglobin A1c, the amount of the binding of the antibody to the denatured site of the hemoglobin A1c correlating directly to the amount of hemoglobin derivative,
   wherein the metal salt is present in an amount sufficient to accelerate the denaturation of the hemoglobin and includes at least one metal ion selected from the group consisting of sodium (Na), potassium (K), magnesium (Mg) and calcium (Ca).

3. The method for measuring a hemoglobin derivative according to claim 2, wherein
   a concentration of the metal salt is a concentration at which the immunoassay of the hemoglobin A1c as a hemoglobin derivative is not significantly inhibited.

4. The method for measuring a hemoglobin derivative according to claim 2, further comprising
   calculating a ratio of the hemoglobin A1c as a hemoglobin derivative in the hemoglobin.

5. The method of claim 2, wherein determining the amount of the hemoglobin derivative includes adding an agglutinating reagent and measuring an amount of aggregates that are generated from binding of the agglutinating reagent to unbound antibody so as to determine the amount of the hemoglobin derivative.

6. A reagent composition for treating a sample containing a blood component including red blood cells in measuring hemoglobin in the sample, comprising
   a nonionic surfactant, an oxidizing agent and a metal salt for denaturing the hemoglobin,
   wherein the metal salt is present in an amount sufficient to accelerate the denaturation of the hemoglobin and includes at least one metal ion selected from the group consisting of sodium (Na), potassium (K), magnesium (Mg) and calcium (Ca).

7. A reagent composition for treating a sample containing a blood component including red blood cells in measuring hemoglobin and hemoglobin A1c as a hemoglobin derivative in the sample, comprising
- a nonionic surfactant, an oxidizing agent, and a metal salt for denaturing the hemoglobin and the hemoglobin A1c as a hemoglobin derivative, and an antibody specifically binding to a denatured site of the hemoglobin A1c as the denatured hemoglobin derivative,
- wherein the metal salt is present in an amount sufficient to accelerate the denaturation of the hemoglobin and includes at least one metal ion selected from the group consisting of sodium (Na), potassium (K), magnesium (Mg) and calcium (Ca).

8. The reagent composition according to claim 7, wherein a concentration of the metal salt is a concentration at which an immunoassay of the hemoglobin A1c as a hemoglobin derivative is not significantly inhibited.

9. A measurement kit for use in measuring hemoglobin in a sample containing a blood component including red blood cells, comprising
- a reagent composition containing a nonionic surfactant, an oxidizing agent and a metal salt for denaturing the hemoglobin,
- wherein the metal salt is present in an amount sufficient to accelerate the denaturation of the hemoglobin and includes at least one metal ion selected from the group consisting of sodium (Na), potassium (K), magnesium (Mg) and calcium (Ca).

10. A measurement kit for use in measuring hemoglobin and hemoglobin A1c as a hemoglobin derivative in a sample containing a blood component including red blood cells, comprising
- a reagent composition containing a nonionic surfactant, an oxidizing agent, and a metal salt for denaturing the hemoglobin and the hemoglobin A1c as a hemoglobin derivative, and an antibody specifically binding to a denatured site of the hemoglobin A1c as the hemoglobin derivative denatured by the reagent composition,
- wherein the metal salt is present in an amount sufficient to accelerate the denaturation of the hemoglobin and includes at least one metal ion selected from the group consisting of sodium (Na), potassium (K), magnesium (Mg) and calcium (Ca).

11. The measurement kit according to claim 10, wherein a concentration of the metal salt is a concentration at which an immunoassay of the hemoglobin A1c as a hemoglobin derivative is not significantly inhibited.

12. An analysis device for use in measuring hemoglobin in a sample containing a blood component including red blood cells, comprising:
- a sample addition site for adding the sample;
- a denaturation section connected to the sample addition site, for denaturing the hemoglobin in the added sample with a reagent composition containing a nonionic surfactant, an oxidizing agent and a metal salt, wherein the denaturation section comprises the reagent composition, and
- a detection section connected to the denaturation section, for detecting the denatured hemoglobin,
- wherein the metal salt included in the reagent composition is present in an amount sufficient to accelerate the denaturation of the hemoglobin and includes at least one metal ion selected from the group consisting of sodium (Na), potassium (K), magnesium (Mg) and calcium (Ca).

13. An analysis device for use in measuring hemoglobin and hemoglobin A1c as a hemoglobin derivative in a sample containing a blood component including red blood cells, comprising:
- a sample addition site for adding the sample,
- a denaturation section connected to the sample addition site, for denaturing hemoglobin in the added sample with a reagent composition containing at least a nonionic surfactant, an oxidizing agent and a metal salt, wherein the denaturation section comprises the reagent composition;
- a hemoglobin detection section connected to the denaturation section, for detecting the denatured hemoglobin;
- an immunoassay section retaining an antibody specifically binding to a denatured site of hemoglobin A1c as a hemoglobin derivative denatured, and
- a hemoglobin derivative detection section for detecting the denatured hemoglobin A1c as a hemoglobin derivative after the hemoglobin A1c as a hemoglobin derivative is denatured by the reagent composition, the hemoglobin derivative detection section performing an immunoassay using the antibody for the detection,
- wherein the metal salt included in the reagent composition is present in an amount sufficient to accelerate the denaturation of the hemoglobin and includes at least one metal ion selected from the group consisting of sodium (Na), potassium (K), magnesium (Mg) and calcium (Ca),
- wherein the denaturation section, the hemoglobin detection section, the immunoassay section and the hemoglobin derivative detection section are in fluid communication with one another.

14. The analysis device according to claim 13, wherein a concentration of the metal salt included in the reagent composition retained in the denaturation section is a concentration at which the immunoassay of the hemoglobin A1c as a hemoglobin derivative is not significantly inhibited.

15. The analysis device according to claim 13, wherein a ratio of the hemoglobin A1c as a hemoglobin derivative in the hemoglobin denatured in the denaturation section is calculated.

16. The analysis device according to claim 13, further comprising
- a measurement section for optically measuring an amount of the hemoglobin detected by the hemoglobin detection section and an amount of the hemoglobin A1c as a hemoglobin derivative detected by the hemoglobin derivative detection section of the analysis device.

* * * * *